(12) United States Patent
Saleh

(10) Patent No.: US 10,883,906 B2
(45) Date of Patent: Jan. 5, 2021

(54) APPARATUS AND METHOD FOR TESTING A PAVEMENT SPECIMEN

(71) Applicant: The University of Canterbury, Christchurch (NZ)

(72) Inventor: Mofreh Saleh, Christchurch (NZ)

(73) Assignee: UNIVERSITY OF CANTERBURY, Christchurch (NZ)

(*) Notice: Subject to any disclaimer, the term of this patent is extended or adjusted under 35 U.S.C. 154(b) by 233 days.

(21) Appl. No.: 16/309,988

(22) PCT Filed: Jun. 28, 2017

(86) PCT No.: PCT/NZ2017/050088
§ 371 (c)(1),
(2) Date: Dec. 14, 2018

(87) PCT Pub. No.: WO2018/004360
PCT Pub. Date: Jan. 4, 2018

(65) Prior Publication Data
US 2019/0323933 A1    Oct. 24, 2019

(30) Foreign Application Priority Data
Jun. 30, 2016 (NZ) ........................ 721765

(51) Int. Cl.
*G01N 3/34* (2006.01)
*G01N 3/56* (2006.01)
(Continued)

(52) U.S. Cl.
CPC ............... *G01N 3/34* (2013.01); *G01N 3/56* (2013.01); *G01N 19/00* (2013.01); *E01C 7/14* (2013.01); *G01N 33/42* (2013.01)

(58) Field of Classification Search
CPC ........... G01N 3/34; G01N 3/56; G01N 19/00; G01N 33/42; E01C 7/14
(Continued)

(56) References Cited

U.S. PATENT DOCUMENTS 5,659,140 A * 8/1997 Jakob ..................... G01N 3/56
                                                              73/788
5,969,261 A    10/1999 McAlister et al.
(Continued)

FOREIGN PATENT DOCUMENTS

CN        201402236 Y    2/2010
CN        204789129      11/2015
(Continued)

OTHER PUBLICATIONS

Extended European Search Report dated Feb. 3, 2020 for corresponding European Application No. 17820611.6 (6 pages).
(Continued)

*Primary Examiner* — Robert R Raevis
(74) *Attorney, Agent, or Firm* — Michael Best & Friedrich LLP

(57) ABSTRACT

A rut testing apparatus for testing the susceptibility of a pavement specimen to rutting has a specimen holder for supporting the specimen to be tested, a wheel, and a sensor. The specimen holder is arranged to support the specimen from below and to support two opposite ends of the specimen. The specimen holder is arranged to allow the specimen to deform in a lateral direction LD that is transverse to a direction that extends between the opposite ends. The wheel is arranged to move along at least part of the specimen in the direction that extends between the opposite ends. The sensor determines deformation of the specimen in the lateral direction LD.

20 Claims, 18 Drawing Sheets

(51) Int. Cl.
  *G01N 19/00* (2006.01)
  *E01C 7/14* (2006.01)
  *G01N 33/42* (2006.01)
(58) Field of Classification Search
  USPC ..... 73/8, 786, 788, 790, 806, 808, 810, 813, 73/818, 821, 822, 856, 146
  See application file for complete search history.

(56) References Cited

U.S. PATENT DOCUMENTS

| | | | |
|---|---|---|---|
| 6,125,685 | A | 10/2000 | Collier et al. |
| 9,234,825 | B2 | 1/2016 | Huang et al. |
| 2015/0292989 | A1 | 10/2015 | Regimand et al. |
| 2019/0033189 | A1* | 1/2019 | Coe .................. G01N 3/32 |

FOREIGN PATENT DOCUMENTS

| | | |
|---|---|---|
| CN | 204789191 | 11/2015 |
| CN | 204789201 | 11/2015 |
| EP | 825439 | 2/1998 |
| JP | 10-185908 | 7/1998 |
| KR | 101233058 | 2/2013 |

OTHER PUBLICATIONS

Aashto, "Standard T 324-17: Standard Method of Test for Hamburg Wheel-Track Testing of Compacted Asphalt Mixtures," Technical Section: 2c, Asphalt—Aggregate Mixtures; Release: Group 3 (Aug. 2017).

Ahmad, "Rutting Evaluation of Dense Graded Hot Mix Asphalt Mixture," International Journal of Engineering & Technology 11(05) (2011).

Archilla et al., "Development of a pavement rutting model from experimental data," Journal of Transportation Engineering, 126(4), 291-299. doi: 10.1061/(asce)0733-947x(2000)126:4(291) (2000).

ARRB Group, "Commentary to AG:PT/T-220—Sample Preparation—Compaction of Asphalt Slabs Suitable for Characterisation. Sydney," Standards Australia (2005).

ARRB Group, "Guide to Pavement Technology Part 2: Pavement Structural Design," ISBN 978-1-921991-11-0, Sydney, Australia (2012).

Australian Standard, "Methods of Sampling and Testing Asphalt," vol. AS 2891.2.1, Sydney: Standards Australia (1995).

Azari et al: "Precision of Hamburg Wheel-Track Test (AASHTO T 324) Draft", Transportation Research Board TRB Annual Meeting (Jan. 2015).

Biligiri et al., "Rational Modeling of Tertiary Flow for Asphalt Mixtures," Transportation Research Record: Journal of the Transportation Research Board, 63-67 (2007).

Francken et al., "L. Pavement Deformation Law of Bituminous Road Mixes in Repeated Load Triaxial Compression," Proceedings of the fourth International Conference on the Structural Design of Asphalt Pavements, vol. I. The University of Michigan, Ann Arbor, Michigan, 483-496 (1977).

Kandhal, "Accelerated Laboratory Rutting tests: Evaluation of the Asphalt Pavement Analyzer," Washington D.C. (2003).

Lu, "Evaluation of Hamburg Wheel-Tracking Device Test with Laboratory and Field Performance Data," Transportation Research Record: Journal of the Transportation Research Board V (2006).

Shami et al., "Development of Temperature-Effect Model for Predicting Rutting of Asphalt Mixtures Using Georgia Loaded Wheel Tester," Transportation Research Record (1997).

Witczak, "Simple Performance Test for Superpave Mix Design," Washington, D.C. (2002).

Witczak, "Simple Performance Tests: Summary of Recommended Methods and Database," Washington, D.C., Transportation Research Board (2005).

Witczak, "Specification Criteria for Simple Performance Tests for Rutting vol. I: Dynamic Modulus (E*) vol. II, Flow Number and Flow Time," Washington, D.C. (2007).

Xu et al, "Evaluation of permanent deformation of asphalt mixtures using different laboratory performance tests," Construction and Building Materials 53, p. 561-567 (2014).

Yildirim et al, "Analysis of Hamburg Wheel Tracking Device Results in Relation to Field Performance," Report No. FHWA/TX-06/0/4185-5, Center for Transportation Research, The University of Texas at Austin (Jul. 2006).

Rahman et al., "Review and Analysis of Hamburg Wheel Tracking Device Test Data," Report No. KS-14-1, Kansas Department of Transportation Topeka, Kansas, p. 1-73 (Feb. 2014).

Yildirim et al., "Hamburg Wheel-Tracking Database Analysis," Report No. FHWA/TX-05/0-1707-7, Texas Transportation Institute the Texas A&M University System College Station, Texas 77843-3135, p. 1-136 (Nov. 2007).

Uzarowski et al., "Accelerated Performance Testing of Canadian Asphalt Mixes Using Three Different Wheel Rut Testers," Annual Conference and Exhibition of the Transportation Association of Canada, p. 1-15 (2004).

PCT/NZ2017/050088 International Search Report and Written Opinion of the International Searching Authority dated Sep. 6, 2017 (9 pages).

* cited by examiner

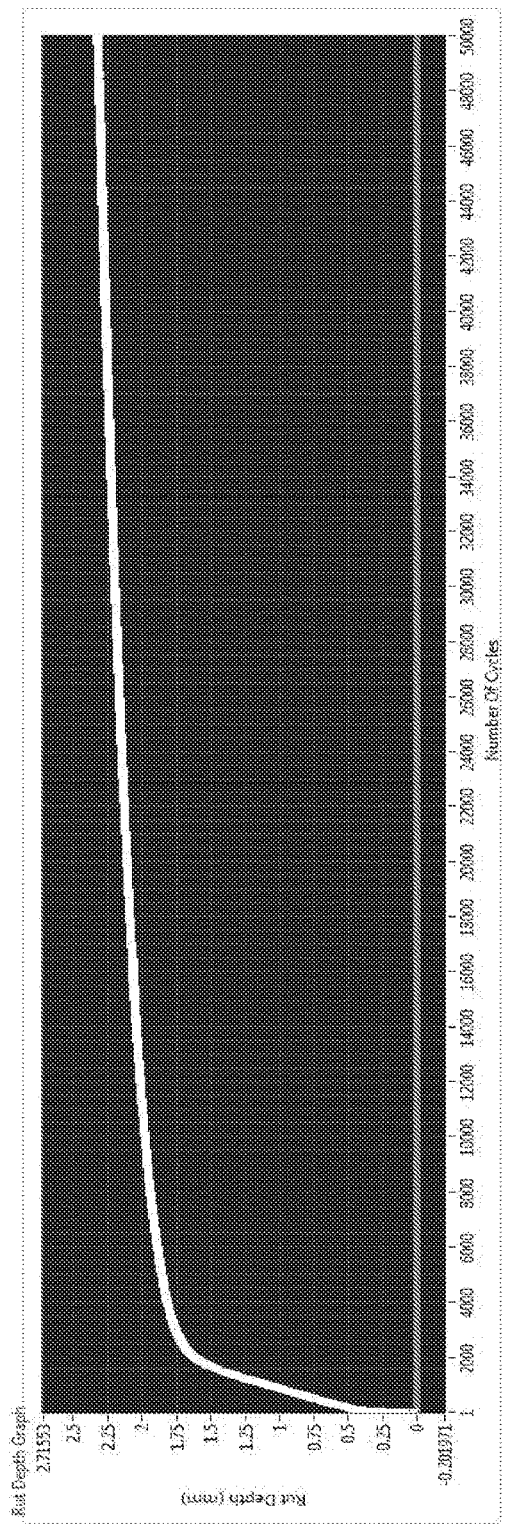
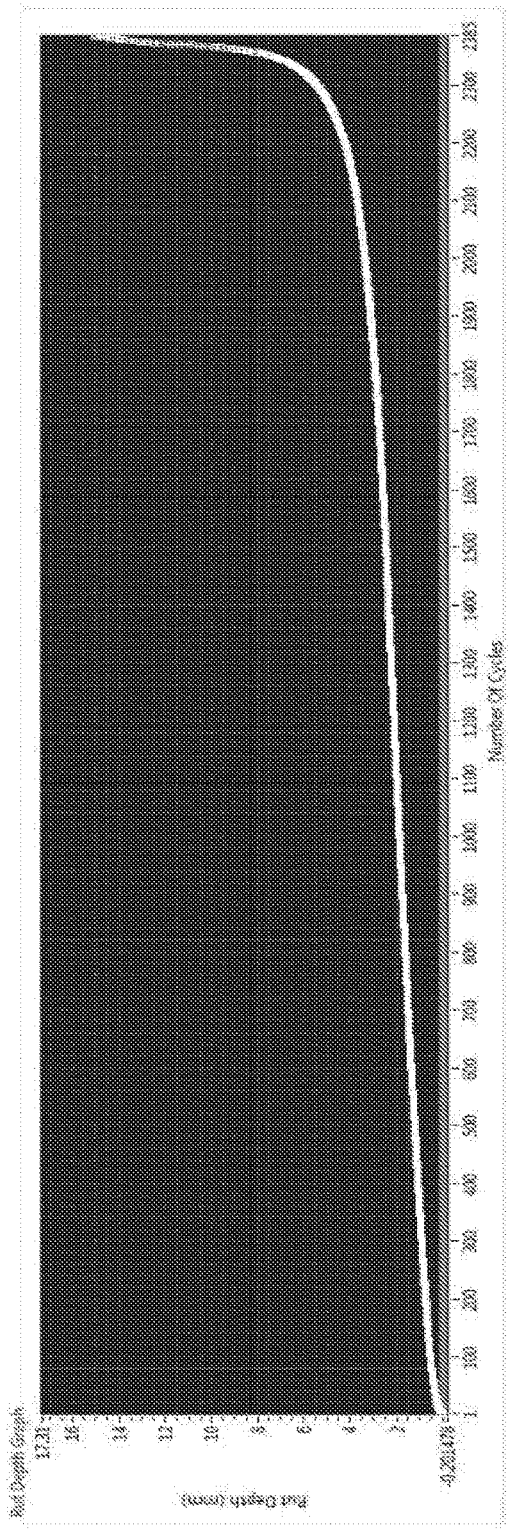
*FIGURE 9A*
*FIGURE 9B*

APPARATUS AND METHOD FOR TESTING A PAVEMENT SPECIMEN

FIELD OF THE INVENTION

This invention relates to an apparatus and method for testing a pavement specimen. In particular, the invention relates to an apparatus and method for testing the susceptibility of a pavement specimen to rutting.

BACKGROUND

Rutting is classified as one of the primary structural deteriorations criteria in flexible pavements design [reference 1]. The distress can be divided principally into three mechanisms; one dimensional deformation, mechanical deformation and lateral flow or plastic movement. Plastic deformation is the major type of permanent deformation caused by inadequate shear strength. Severe rutting is a result of this mechanism [reference 2].

An existing test for asphalt material behaviour is the Simple Performance Test (SPT) [references 3 and 4]. The SPT uses repeated and/or static creep tests to measure shear deformation. Asphalt material response under repeated load application results in a permanent deformation curve that can be divided into three major zones known as primary, secondary and tertiary zones. In general, permanent deformation accumulates at a decreasing rate in the primary zone. The rate of decrease reaches a constant value in the secondary zone and increases rapidly at the onset of the tertiary zone [reference 4]. The inflection point between the secondary and tertiary zones is referred to as the flow number on the deformation vs number of cycle curve or the flow time on the deformation vs time relationship. The tertiary inflection point has two significant characteristics. First, permanent deformation rate undergoes a dramatic increase after the tertiary inflection point. Second, it occurs under a constant volume which indicates pure shear (plastic) deformation.

SPT tests have several disadvantages. They are time consuming and they require elaborate testing equipment. In addition, they are not suitable for quality control and quality assurance (QC/QA). A major disadvantage is that none of the test loading sequences is close to the actual traffic loading. As a result, other types of test apparatuses have been developed with less sophisticated test mechanisms which better represent actual traffic loading that can be used for QC/QA of pavement construction [reference 5].

A test that can be used to better simulate the action of moving traffic wheel is the wheel tracker test [references 6 and 7].

FIG. 1 illustrates a conventional wheel tracker test setup. An asphalt specimen 101 is held in a specimen holder 103 on a moving table that reciprocates beneath a vertically loaded wheel 102. The specimen is fully constrained by the specimen holder by fixed supports 110, 111, 120, 121 at all four sides of the specimen; that is, the specimen is fully constrained. The vertical displacement of the specimen is measured as the rut depth develops in the specimen. The test ends either when a maximum number of cycles is reached or when a maximum rut depth is reached, whichever occurs first.

A significant disadvantage of the conventional wheel tracker test is that it rarely reaches the tertiary zone. The results are also difficult to analyse.

Table 1 shows the results of conventional wheel tracker tests conducted by the inventor using the apparatus of FIG. 1. Six specimens were prepared with different binder types (60/70 and 80/100), different aggregate gradations (maximum nominal sizes, 14 mm and 20 mm), and different air voids content (ranging from 4.3% to 7.7%). The tests were conducted at high temperatures (either 50° C. or 60° C.) for 50,000 cycles and the total permanent vertical deformations were recorded.

TABLE 1

Conventional fully constrained wheel tracker test results

| Gradation | Binder Type | Air Void % | Temperature ° C. | Rutting-mm |
|---|---|---|---|---|
| AC 14 | 60/70 | 5.50 | 50.0 | 2.1 |
| AC 20 | 80/100 | 5.00 | 50.0 | 2.3 |
| AC 20 | 60/70 | 7.70 | 50.0 | 2.2 |
| AC 14 | 80/100 | 6.30 | 60.0 | 2.4 |
| AC 20 | 80/100 | 5.60 | 50.0 | 2.5 |
| AC 20 | 60/70 | 4.30 | 60.0 | 2.0 |

Table 1 shows that the total permanent deformations accumulated after 50,000 cycles at 50° C. and 60° C. are quite small and not significantly different regardless of the aggregate gradation, binder type or test temperature. Therefore, the tertiary stage for rutting is unlikely to be reached using the conventional fully constrained test setup. The wheel tracker test results for the fully constrained specimens are difficult to analyse as the differences in rutting depth between the specimens are so small that it is not possible to accurately rank the permanent deformation resistance of the tested mixes.

Based on the test results shown in Table 1, one could incorrectly conclude that changes of the major mix parameters and test conditions have no significant effect on the permanent deformation of the tested mixes. The unrealistic constraining stresses caused by the walls of the specimen holder cause the final permanent deformations to be much smaller than what could be achieved under a more realistic constraining condition. Researchers have observed this disadvantage with the wheel tracker test [references 11 and 12].

An object of at least preferred embodiments of the present invention is to provide a rut testing apparatus and/or method that better simulates actual constraining stresses and is capable of determining tertiary zone shear failure. It is an additional or alternative object of at least preferred embodiments of the present invention to at least provide the public with a useful choice.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

SUMMARY OF THE INVENTION

In accordance with a first aspect of the present invention, there is provided a rut testing apparatus for testing the susceptibility of a pavement specimen to rutting, the apparatus comprising: a specimen holder for supporting the specimen to be tested, the specimen holder arranged to support the specimen from below and to support two opposite ends of the specimen, the specimen holder arranged so that one or more lateral sides of the specimen are substantially unsupported or supported by a moveable support member to allow the specimen to deform in a lateral direction that is transverse to a direction that extends between the opposite ends for substantially an entire test; a wheel that is arranged to move along at least part of the specimen in the direction that extends between the opposite ends; and a sensor to determine deformation of the specimen in the lateral direction.

In an embodiment, the specimen holder is arranged so that two lateral sides of the specimen are substantially unsupported during testing. The lateral sides may be parallel to the direction of movement of the wheel, or may be offset from parallel. The specimen, and specimen holder, may be any suitable shape, such as square, rectangular, circular, or any other suitable shape.

In an embodiment, the specimen holder comprises a first moveable support member to support a first lateral side of the specimen, the first movable support member arranged to allow deformation of the specimen in the lateral direction. In an embodiment, the specimen holder comprises a fixed support member to support a second opposite lateral side of the specimen.

In an embodiment, the specimen holder comprises a second moveable support member to support a second opposite lateral side of the specimen, the second moveable support member arranged to allow deformation of the specimen in the lateral direction.

In an embodiment, the apparatus comprises a second sensor associated with the second lateral side to determine deformation of the specimen in the lateral direction.

In an embodiment, at least one sensor comprises a dial test indicator.

In an embodiment, at least one sensor comprises a linear variable differential transformer.

In an embodiment, the specimen holder comprises a first end moveable support member to support a first end of the specimen, the first end moveable support member arranged to allow deformation of the specimen in the direction that extends between the opposite ends. In an embodiment, the specimen holder comprises a fixed end support member to support a second opposite end of the specimen. Alternatively, the specimen holder may comprise a second end moveable support member to support a second opposite end of the specimen, the second end moveable support member arranged to allow deformation of the specimen in the direction that extends between the opposite ends.

In an embodiment, the position of the moveable support member(s) is controlled to provide substantially constant pressure to the sides and/or ends of the specimen during testing.

In an embodiment, the apparatus comprises a sensor to determine deformation of the specimen in a direction that is generally orthogonal to the direction that extends between the opposite ends and to the lateral direction; i.e. a generally downwards direction. In an embodiment, the sensor comprises a linear variable differential transformer.

In an embodiment, the apparatus comprises a processor configured to provide a graphical representation of deformation in the lateral direction and/or in a direction that is generally orthogonal to the direction that extends between the opposite ends and to the lateral direction (i.e. in a downward direction). In an embodiment, the graphical representation shows the rate of change of permanent deformation in the lateral direction.

In an embodiment, the graphical representation shows the rate of change of permanent deformation in the direction that is generally orthogonal to the direction that extends between the opposite ends and to the lateral direction; i.e. downward vertical deformation if a base of the specimen holder that supports the specimen from below is horizontal. In an embodiment, the graphical representation shows the number of cycles at which permanent deformation in both directions progresses at the same rate.

In an embodiment, the apparatus comprises a processor configured to determine the extent of deformation in the lateral direction and/or in a direction that is generally orthogonal to the direction that extends between the opposite ends and to the lateral direction. In an embodiment, the processor is configured to determine the rate of change of permanent deformation in the lateral direction. In an embodiment, the processor is configured to determine the rate of change of permanent deformation in the direction that is generally orthogonal to the direction that extends between the opposite ends and to the lateral direction; i.e. a downward direction. In an embodiment, the processor is configured to determine the number of cycles at which permanent deformation in both directions progresses at the same rate.

In an embodiment, the processor is configured to determine or estimate permanent deformation in the direction that is generally orthogonal to the direction that extends between the opposite ends and to the lateral direction, based on the determined permanent deformation in the lateral direction.

In an embodiment, the lateral direction is substantially orthogonal to the direction that extends between the opposite ends.

The apparatus may comprise a temperature controlled environment for the specimen. The temperature controlled environment may comprise a temperature cabinet.

In accordance with a second aspect of the present invention, there is provided a method of testing the susceptibility of a pavement specimen to rutting, the method comprising: supporting a pavement specimen in a specimen holder, the specimen holder arranged to support the specimen from below and to support two opposite ends of the specimen, the specimen holder arranged so that one or more lateral sides of the specimen are substantially unsupported or supported by a moveable support member to allow the specimen to deform in a lateral direction that is transverse to a direction that extends between the opposite ends for substantially an entire test; moving a wheel along at least part of the specimen in the direction that extends between the opposite ends; and measuring deformation of the specimen in the lateral direction.

In an embodiment, said supporting a pavement specimen comprises having two lateral sides of the specimen substantially unsupported.

In an embodiment, the method comprises supporting a first lateral side of the specimen with a first moveable support member, wherein the first movable support member is arranged to allow deformation of the specimen in the lateral direction. In an embodiment, the method comprises supporting a second opposite lateral side of the specimen with a fixed support member. In an embodiment, the method comprises supporting a second opposite lateral side of the specimen with a second moveable support member, wherein the second moveable support member is arranged to allow deformation of the specimen in the lateral direction.

In an embodiment, the method comprises measuring the lateral deformation of the lateral side(s) of the specimen with a dial test indicator.

In an embodiment, the method comprises measuring the lateral deformation of the lateral side(s) of the specimen with a linear variable differential transformer.

In an embodiment, the method comprises supporting a first end of the specimen with a first end moveable support member, the first end moveable support member arranged to allow deformation of the specimen in the direction that extends between the opposite ends. In an embodiment, the method comprises supporting a second opposite end of the specimen with a fixed end support member. Alternatively, the method may comprise supporting a second opposite end of the specimen with a second end moveable support member, the second end moveable support member arranged to allow deformation of the specimen in the direction that extends between the opposite ends.

In an embodiment, the method comprises controlling the position of the moveable support member(s) to provide substantially constant pressure to the sides and/or ends of the specimen during testing.

In an embodiment, the method comprises measuring deformation of the specimen in a direction that is generally orthogonal to the direction that extends between the opposite ends and to the lateral direction; i.e. a downward direction. In an embodiment, the method comprises measuring deformation of the specimen with a linear variable differential transformer.

In an embodiment, the method comprises using a processor to provide a graphical representation of deformation in the lateral direction and/or in a direction that is generally orthogonal to the direction that extends between the opposite ends and to the lateral direction (i.e. in a downward direction).

In an embodiment, the graphical representation shows the rate of change of permanent deformation in the lateral direction. In an embodiment, the graphical representation shows the rate of change of permanent deformation in the direction that is generally orthogonal to the direction that extends between the opposite ends and to the lateral direction.

In an embodiment, the graphical representation shows the number of cycles at which permanent deformation in both directions progresses at the same rate.

In an embodiment, the method comprises using a processor to determine the extent of deformation in the lateral direction and/or in a direction that is generally orthogonal to the direction that extends between the opposite ends and to the lateral direction. In an embodiment, the processor is configured to determine the rate of change of permanent deformation in the lateral direction. In an embodiment, the processor is configured to determine the rate of change of permanent deformation in the direction that is generally orthogonal to the direction that extends between the opposite ends and to the lateral direction. In an embodiment, the processor is configured to determine the number of cycles at which permanent deformation in both directions progresses at the same rate.

In an embodiment, the method comprises determining or estimating permanent deformation in the direction that is generally orthogonal to the direction that extends between the opposite ends and to the lateral direction, based on the determined permanent deformation in the lateral direction.

In an embodiment, the method comprises the lateral direction is substantially orthogonal to the direction that extends between the opposite ends.

In an embodiment, the method comprises placing the specimen in a temperature controlled environment for the test. The temperature controlled environment may comprise a temperature cabinet.

In an embodiment, the method is performed using an apparatus as outlined in relation to the first aspect above.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

The terms 'component', 'module', 'system', 'interface', and/or the like as used in this specification in relation to a processor are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The term 'connected to' as used in this specification in relation to data or signal transfer includes all direct or indirect types of communication, including wired and wireless, via a cellular network, via a data bus, or any other computer structure. It is envisaged that they may be intervening elements between the connected integers. Variants such as 'in communication with', 'joined to', and 'attached to' are to be interpreted in a similar manner. Related terms such as 'connecting' and 'in connection with' are to be interpreted in the same manner.

BRIEF DESCRIPTION OF THE DRAWINGS

The present invention will now be described by way of example only and with reference to the accompanying drawings in which:

FIG. 9A shows a graph of results from a fully constrained test using the apparatus of FIG. 1—AC20, 80/100 binder, 6.0% air voids, 50° C.;

FIG. 9B shows a graph of results from a partially constrained test using the apparatus of FIGS. 2 and 3—AC20, 80/100 binder, 6.0% air voids, 50° C.;

DETAILED DESCRIPTION OF PREFERRED EMBODIMENTS

In preferred embodiments of the invention, the pavement specimen is partially constrained in the specimen holder. One or more lateral sides of the partially constrained specimen are either substantially unsupported, or supported by a moveable support member. In some embodiments, one or more ends of the partially constrained specimen are supported by a moveable support member.

Unconstrained Lateral Sides

Figure 2:
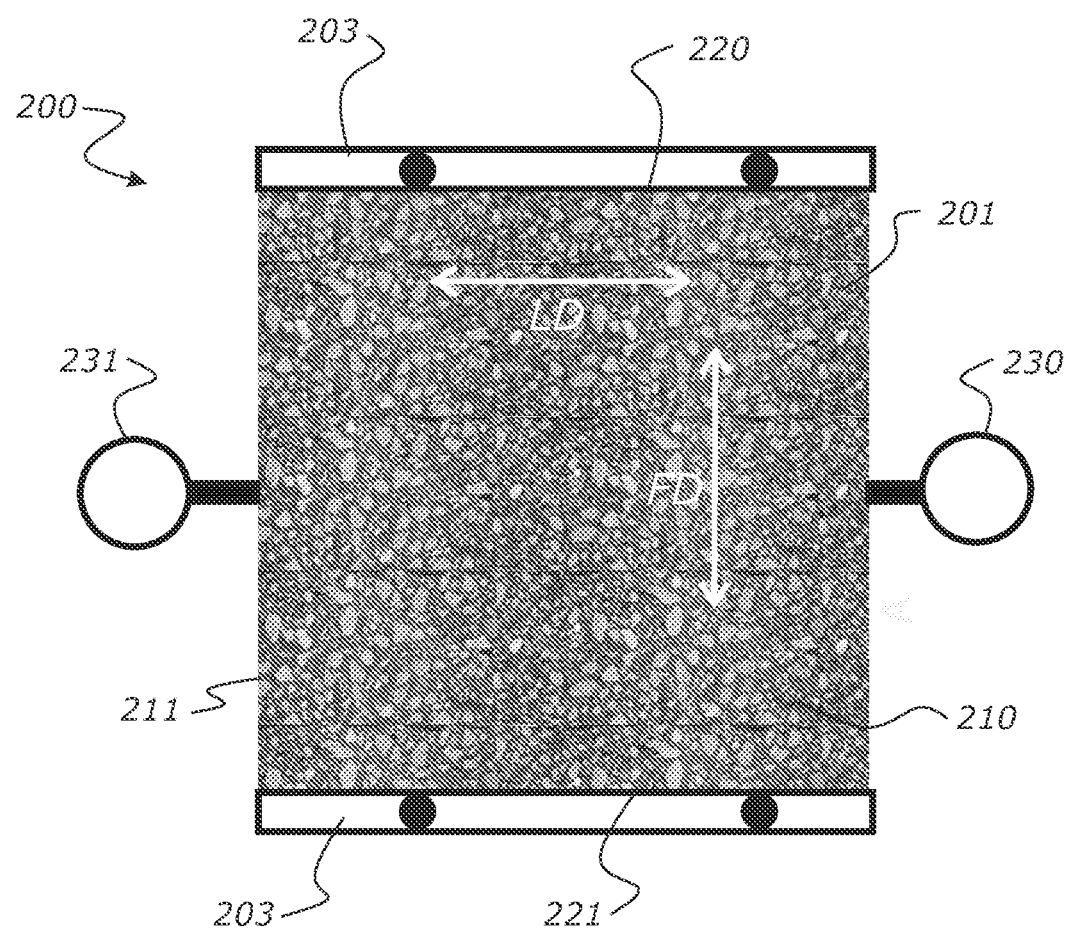
FIG. 2 shows a schematic view of a first embodiment rut testing apparatus with unconstrained lateral sides.
Figure 3:
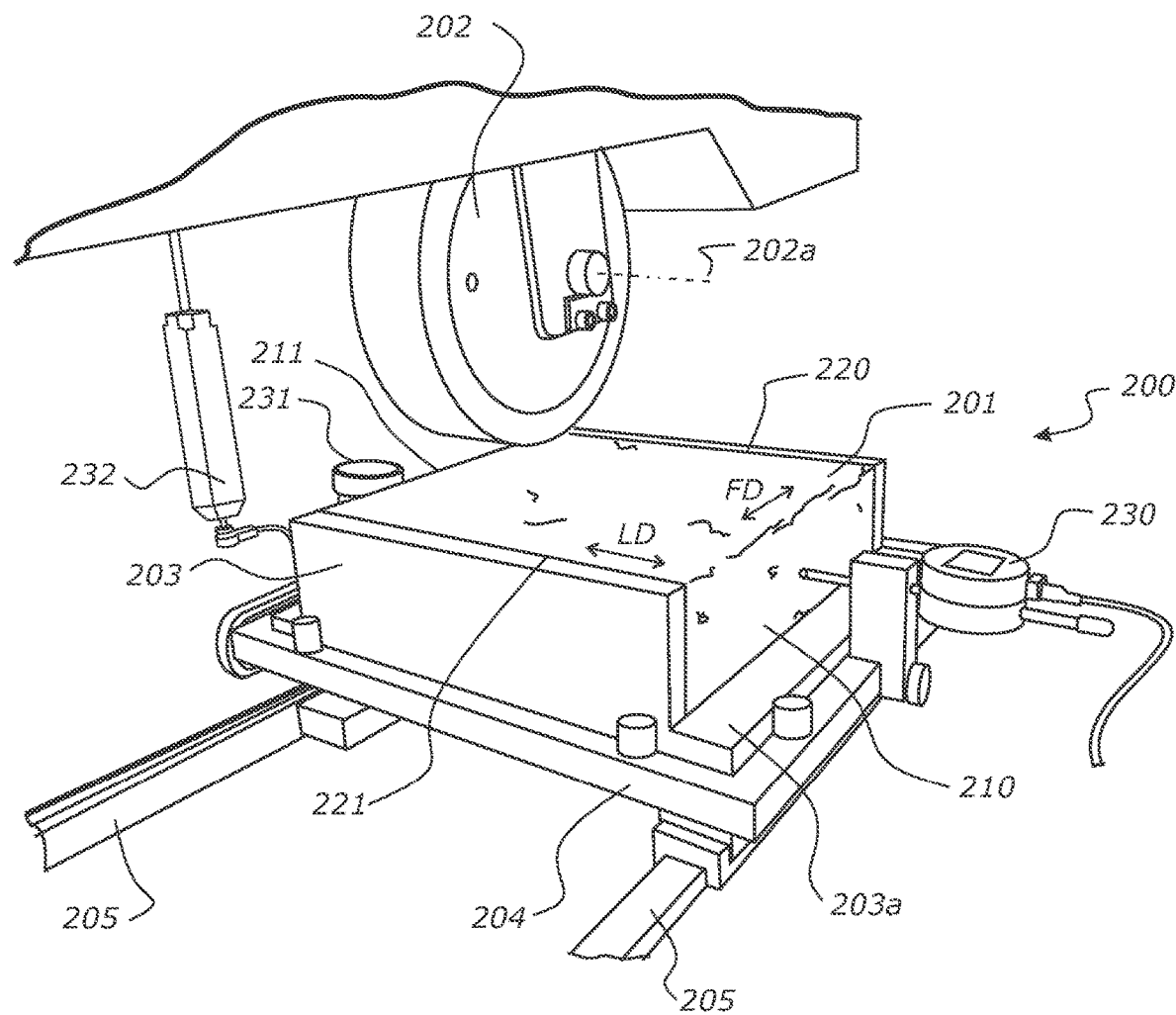
FIG. 3 shows the rut testing apparatus of FIG. 2.

FIGS. 2 and 3 show a rut testing apparatus 200 in accordance with a first embodiment for testing the susceptibility of a pavement specimen 201 to permanent deformation (rutting). The apparatus comprises a specimen holder 203 for supporting the specimen 201 to be tested, a wheel 202, a first lateral displacement sensor 230, a second lateral displacement sensor 231 and a vertical displacement sensor 232.

Specimen Holder

The specimen holder 203 has a base plate 203a that is arranged to support the specimen 201 from below. The base plate 203a is advantageously at least the size of the specimen to support the underside of the entire specimen. The specimen 201 rests on the base plate 203a during testing. The specimen holder has two end support members 220, 221 in the form of laterally extending plates that are arranged to support two opposite ends of the specimen. In the form shown, the end support members 220, 221 are fixed in position relative to the base plate 203a by upstands that are coupled to the base plate. Alternatively, the end support members 220 could be integrally formed with the base plate 203a.

The specimen holder is arranged so that two lateral sides 210, 211 of the specimen 201 are substantially unsupported (other than by the base plate 203a) during testing. The specimen holder 203 is arranged to allow the specimen 201 to deform in a second lateral direction LD that is transverse to a first direction FD that extends between the end support members 220, 221 that support opposite ends of the specimen. In the form shown, the lateral direction LD is substantially orthogonal to the first direction FD, but that will depend on the shape of the specimen.

In an embodiment, the specimen holder 203 is arranged to allow the specimen 201 to deform in the lateral direction LD for substantially the entire test. In an embodiment, the specimen holder 203 is arranged to allow the specimen 201 to deform in the lateral direction LD for the entire test.

The specimen holder is positioned on a table 204 that is slidably mounted on rails 205. The table, and thereby the specimen holder 203, is driven to reciprocate back and forth on the rails 205 by a suitable driving device such as hydraulic ram(s) or motor(s) for example.

The specimen holder components can be made from any suitable material that is compatible with the specimen being tested, such as stainless steel for example.

Wheel

The wheel 202 is rotatable around a rotation axis 202a. The wheel comprises a suitable resilient peripheral material such as rubber for example, to enable the wheel to apply load to the specimen 201 while not causing excessive damage to the specimen. The peripheral material on the wheel is chosen to be representative of a vehicle tyre on a road. The wheel is movable in a direction that is orthogonal to a plane that contains the lateral direction LD and the first direction FD (i.e. vertically), with its position and downward force that is applied to the specimen being controlled by a hydraulic ram or other movement device. The wheel 202 is arranged to move along at least part of the specimen 201 in the first direction FD that extends between the opposite ends of the specimen. The movement of the wheel 202 along the specimen 201 occurs as a result of the reciprocation of the table 204 on the rails. In one configuration, the wheel 202 is arranged to move along substantially the entire length of the specimen in the first direction FD, with the end support members 220, 221 arranged to prevent crumbling of the ends of the specimen under the load of the wheel.

In an alternative configuration, the specimen holder 203 and table 204 may be fixed, with the reciprocating movement of the wheel 202 along at least part of the specimen occurring as a result of movement of the wheel 202 rather than movement of the table 204.

The wheel is configured to move at a relatively slow speed of around 26.4 cycles per minute (0.44 Hz). This is representative of vehicle movement at intersections where rutting is prone to occur.

Lateral Displacement Sensor(s)

The lateral displacement sensor(s) 230, 231 is/are arranged to determine deformation of the lateral sides 210, 211 of the specimen in the lateral direction LD. The sensor(s) 230, 231 comprise dial test indicators (DTIs) or any other suitable linear displacement sensor(s.)

Vertical Displacement Sensor(s)

The vertical displacement sensor(s) 232 is/are arranged to determine the deformation of the specimen 201 in a vertical direction. The sensor(s) 232 comprises a linear variable differential transformer (LVDT) or any other suitable linear displacement sensor(s). The vertical displacement sensor(s) 232 is placed on the hydraulic ram or other movement device that controls the downward force applied by the wheel 202. The vertical displacement measurement represents the depth of the rut caused by the wheel 202 tracking across the specimen 201.

Processor

Figure 4:
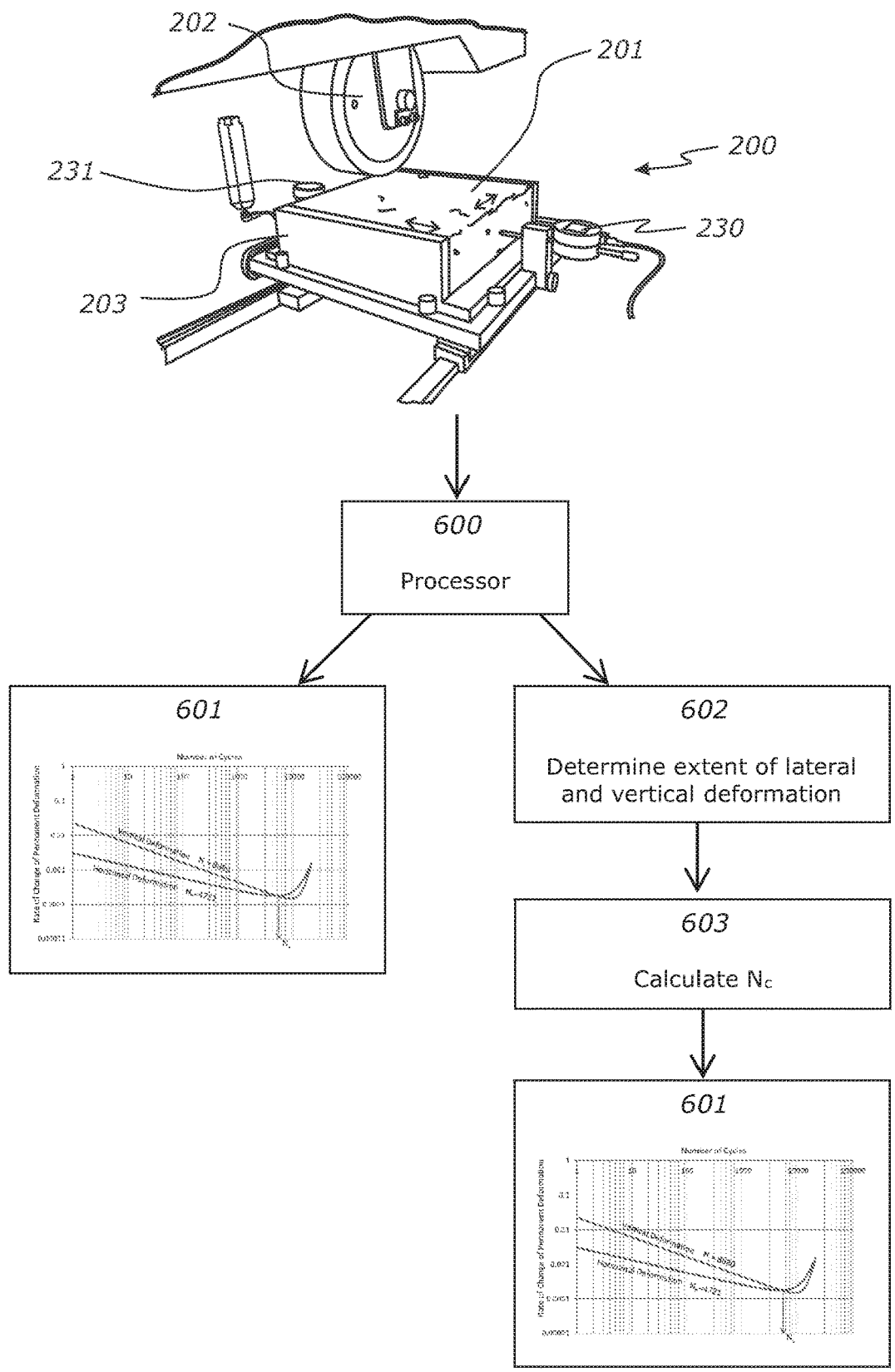
FIG. 4 shows a schematic of a processor and testing method of the apparatus of FIGS. 2 and 3.

The rut testing apparatus 200 comprises a processor 600 as shown schematically in FIG. 4. In an embodiment the processor comprises, forms part of, or is connected to any suitable hardware computing device. Example computing devices include, but are not limited to, personal computers, server computers, hand-held or laptop devices, mobile devices (such as mobile phones. Personal Digital Assistants (PDAs), media players, and the like), multiprocessor systems, consumer electronics, mini computers, mainframe computers, distributed computing environments that include any of the above systems or devices, and the like.

The processor is connected to the lateral displacement sensor(s) 230, 231 and to the vertical displacement sensor(s) 232 and receives signals from those sensors. The processor is configured to perform one or both of the following operations based on those received signals:

Provide a graphical representation of deformation in the lateral direction and/or in the vertical downward direction. For example, the processor may provide a graphical representation 601 of deformation in the vertical downward direction such as those shown in FIGS. 9B and 10B for example. The graphical representation may also show deformation in the lateral direction such as FIG. 11. Additionally or alternatively, the processor may be configured to provide a graphical representation 601 of the rate of change of deformation in the lateral direction such as those shown in FIGS. 12A to 12G. The graphical representation 601 in FIG. 4 shows the rate of change of permanent deformation in the vertical (downward) direction and the rate of change of permanent deformation in the lateral direction. The graphical representation 601 shows the inflection point where tertiary failure starts to occur, known as the flow number (FN). The graphical representation 601 shows different flow numbers for lateral and vertical deformation. These flow numbers can be denoted $N_h$ and $N_v$ respectively. The graphical representation 601 also shows the number of cycles at which both vertical deformation and horizontal deformation progress at the same rate. This point is designated as the critical flow number ($N_c$). The graphical representation may be displayed on a suitable display device, may be printed using a suitable printing device, or may be exported to a storage medium.

Determine the extent of deformation in the lateral direction and/or in the vertical downward direction. For example, the processor may determine the extent of deformation in the lateral direction as shown in FIG. 4. The processor 600 is configured to determine the rate of change of permanent deformation in the vertical (downward) direction and/or the rate of change of permanent deformation in the lateral direction 602. The processor is configured to determine the inflection point of the vertical rate of change of permanent deformation curve (vertical flow number $N_v$) and/or the inflection point of the lateral rate of change of permanent deformation curve (lateral flow number $N_h$), to determine the number of cycles where tertiary failure starts to occur. In an embodiment, the processor is also configured to determine the number of cycles at which both vertical deformation and lateral deformation progress at the same rate 603 (critical flow number $N_c$). The processor can determine these parameters based on suitable numerical calculation methods. The processor 600 optionally also provides a graphical representation 601 as described above.

The processor may be configured to determine or estimate permanent deformation in a direction that is generally orthogonal to the direction that extends between the opposite ends and to the lateral direction, based on the determined permanent deformation in the lateral direction. The processor can determine that based on suitable numerical calculation methods.

More discussion of the operations and parameters that may be determined by the processor is provided in the Comparative Tests section below.

Method

The following method may be performed using the testing apparatus 200 described above.

The method of testing the susceptibility of a pavement specimen to rutting comprises supporting a pavement specimen 201 in the specimen holder 203, moving the wheel 202 along at least part of the specimen 201 in the first direction FD that extends between the opposite ends of the specimen corresponding to the end support members 220, 221, measuring deformation of the specimen 201 in the lateral direction LD, and optionally measuring deformation of the specimen 201 in the vertical direction.

The specimen holder 203 is arranged to support the specimen 201 from below and to support two opposite ends 220, 221 of the specimen. The specimen holder 203 is arranged to allow the specimen 201 to deform in the lateral direction LD that is transverse to a direction that extends between the opposite ends of the specimen.

The step of supporting the pavement specimen 201 comprises having lateral sides 210, 211 of the specimen substantially unsupported.

The lateral deformation of the lateral sides 210, 211 of the specimen 201 is measured with dial test indicator(s) (DTIs) or any other suitable linear displacement sensor(s).

The deformation of the specimen 201 in a vertical (downward) direction is measured with a linear variable differential transformer (LVDT) or any other suitable linear displacement sensor(s).

The method comprises using the processor 600 to perform one or both of the following operations:

Provide a graphical representation of deformation in the lateral direction and/or in the vertical downward direction. For example, the processor may provide a graphical representation 601 of deformation in the lateral direction such as those shown in FIG. 4 or FIGS. 12A to 12G for example. The graphical representation 601 in FIG. 4 shows the rate of change of permanent deformation in the vertical (downward) direction and the rate of change of permanent deformation in the lateral direction. The graphical representation 601 shows the inflection point where tertiary failure starts to occur, known as the flow number (FN). The graphical representation 601 shows different flow numbers for lateral and vertical deformation. These flow numbers can be denoted $N_h$ and $N_v$ respectively. The graphical representation 601 also shows the number of cycles at which both vertical deformation and horizontal deformation progress at the same rate. This point is the critical flow number ($N_c$). The graphical representation may be displayed on a suitable display device, may be printed using a suitable printing device, or may be exported to a storage medium.

Determine the extent of deformation in the lateral direction and/or in the vertical downward direction. For example, the processor may determine the extent of deformation in the lateral direction as shown in FIG. 4. The processor 600 is configured to determine the rate of change of permanent deformation in the vertical (downward) direction and/or the rate of change of permanent deformation in the lateral direction 602. The processor is configured to determine the inflection point of the vertical rate of change of permanent deformation curve (vertical flow number $N_v$) and/or the inflection point of the lateral rate of change of permanent deformation curve (lateral flow number $N_h$), to determine the number of cycles where tertiary failure starts to occur. In an embodiment, the processor is also configured to determine the number of cycles at which both vertical deformation and lateral deformation progress at the same rate 603 (critical flow number $N_c$). The processor can determine that based on suitable numerical calculation methods. The processor 600 optionally also provides a graphical representation 601 as described above.

The method may comprise using the processor to determine or estimate permanent deformation in a direction that is generally orthogonal to the direction that extends between the opposite ends and to the lateral direction, based on the determined permanent deformation in the lateral direction. The processor can determine that based on suitable numerical calculation methods.

Temperature Controlled Environment

The test specimen may be kept in a temperature controlled environment (for example, in a temperature cabinet) during the test. The temperature cabinet can control the temperature up to 70° C. with an accuracy of ±0.1° C. for example.

Comparative Tests

The inventor performed tests to compare the first embodiment rut testing apparatus 200 with a conventional wheel tracker test using the apparatus 100.

Specimen Preparation

Asphalt mixes with 14 and 20 mm nominal maximum aggregate size were prepared. These are commonly used hot mix asphalts in New Zealand. Specimens with dimensions 305×305×50 mm and 305×305×75 mm were prepared for AC 14 and 20, respectively [reference 8]. The aggregates, binders and job mix formula were secured from a local contractor who designed these mixes for one of the heavily trafficked motorways in Christchurch—New Zealand. Asphalt mixtures were prepared based on the Australian standard AS 2891.2.1 'Methods of Sampling and Testing Asphalt' [reference 9]. According to the Australian standards, all mixtures were conditioned at 150° C. for one hour before compaction. The conditioning step simulates short term ageing. After conditioning, the asphalt mixes were compacted at 150° C. The mixtures were compacted to the target air voids content using a roller compactor.

Modified Wheel Tracker Testing Apparatus

A modified version of standard wheel tracker testing apparatus was used for the modified wheel tracker test. The machine includes a single solid rubber wheel. The tyre width is 50±1 mm which applies 700 N load. The average speed is 26.5 cycles per minute. The test is carried out in a temperature controlled chamber.

The modified wheel tracker testing apparatus was designed to permit the specimen to be tested either fully constrained as per the current conventional method, or partially constrained with the specimen supported at two opposite ends and substantially unsupported at the lateral sides as shown in FIG. 2. To record the horizontal deformations, two dial test indicators (DTIs) 230, 231 were mounted on the specimen sides 210, 211. One vertical linear variable differential transformer (LVDT) 232 was also placed under the wheel tracker arm to measure the vertical deformation. The processor/data acquisition system was designed to collect the vertical and the two horizontal deformations with the number of cycles.

Multilayer Analysis of the Constraining Lateral Stresses

Figure 5:
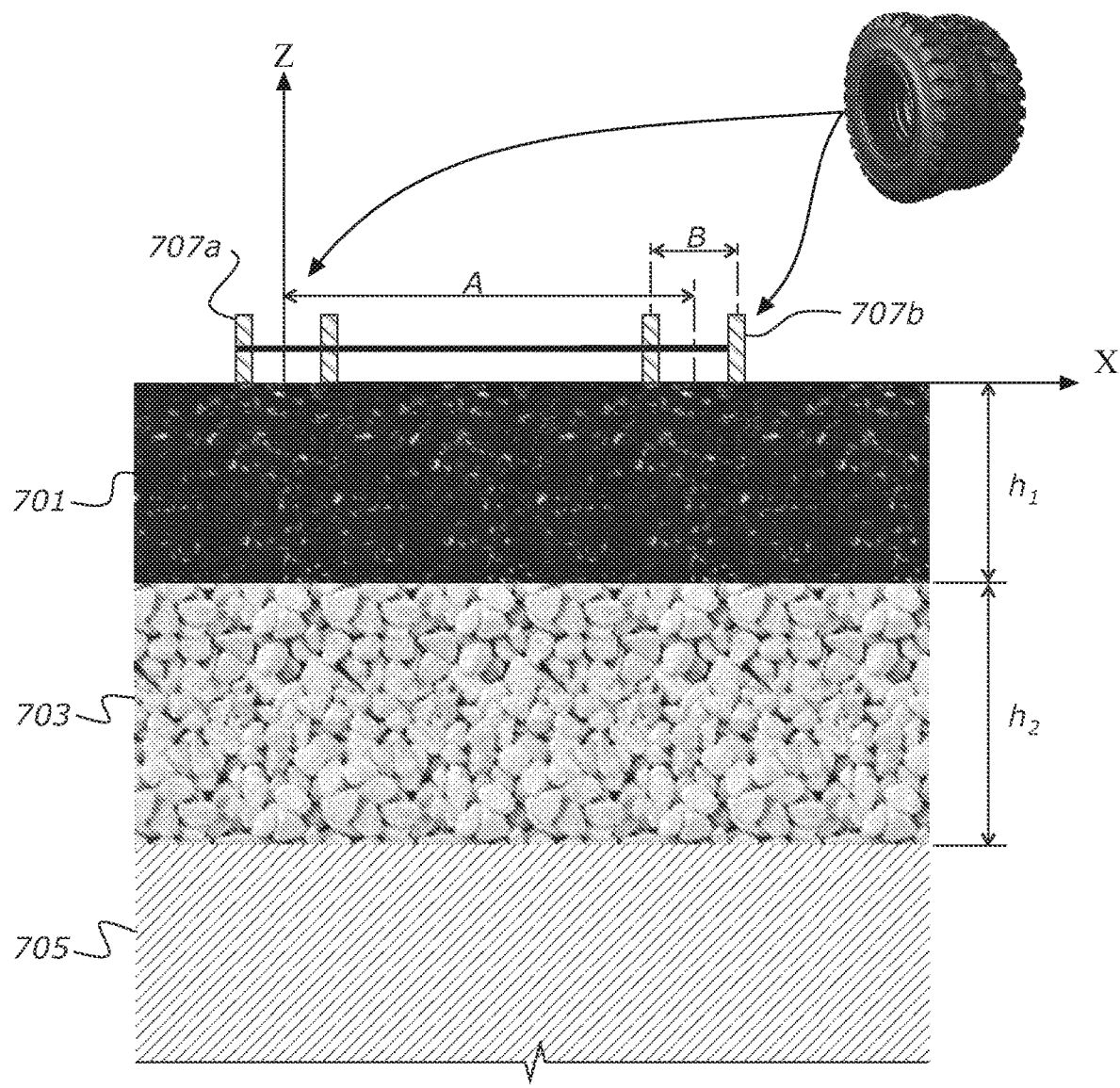
FIG. 5 shows a three layer system under a standard axle load (Circly analysis)

In order to understand the limitations of the current wheel tracker setup and whether there are any significant differences from the actual field conditions, multilayer analysis using Circly software was carried out on a three layer system as shown in FIG. 5. The following parameters were used in the Circly analysis:

Wheels 707a, 707b—the stress analysis was carried out under the effect of a standard 80 kN axle load across two dual tyres 707a, 707b with tyre pressure 750 kPa. The dual tyres 707a, 707b were spaced 1800 mm from each other (dimension A). The tyres within each dual tyre pair were spaced 330 mm apart (dimension B).

Asphalt layer 701—in this analysis, two asphalt moduli (EAC=2000 MPa and EAC=4500 MPa) and two thicknesses of the asphalt layer ($h_1$=100 mm and $h_1$=200 mm) were considered. The reason for selecting these parameters for the asphalt layer 701 was to analyse the stresses for weak and strong structural asphalt layers. In this analysis, the asphalt layer 701 was modelled as isotropic material with a Poisson's ratio of v=0.40. The base layer 703 and subgrade layer 705 were modelled as cross anisotropic material with anisotropic ratio of 0.5

$$\text{anisotropic ratio} = \frac{E_h}{E_v},$$

where $E_h$ is the horizontal modulus and $E_v$ is the vertical modulus) as recommended by Australian guidelines [reference 10]. In order to account for the nonlinearity of the granular base course materials, sub layering was conducted according to Australian guidelines [reference 10].

Base layer 703—the base layer 703 was modelled as having thickness $h_2=400$ mm, vertical modulus $E_v=300$ MPa, horizontal modulus $E_h=0.5$ $E_v$, and Poisson's ratio $v=0.35$.

Subgrade layer 705—the subgrade layer 705 was modelled as having infinite depth, vertical modulus $E_v=50$ MPa, horizontal modulus $E_h=0.5$ $E_v$, and Poisson's ratio $v=0.45$.

Figure 6:
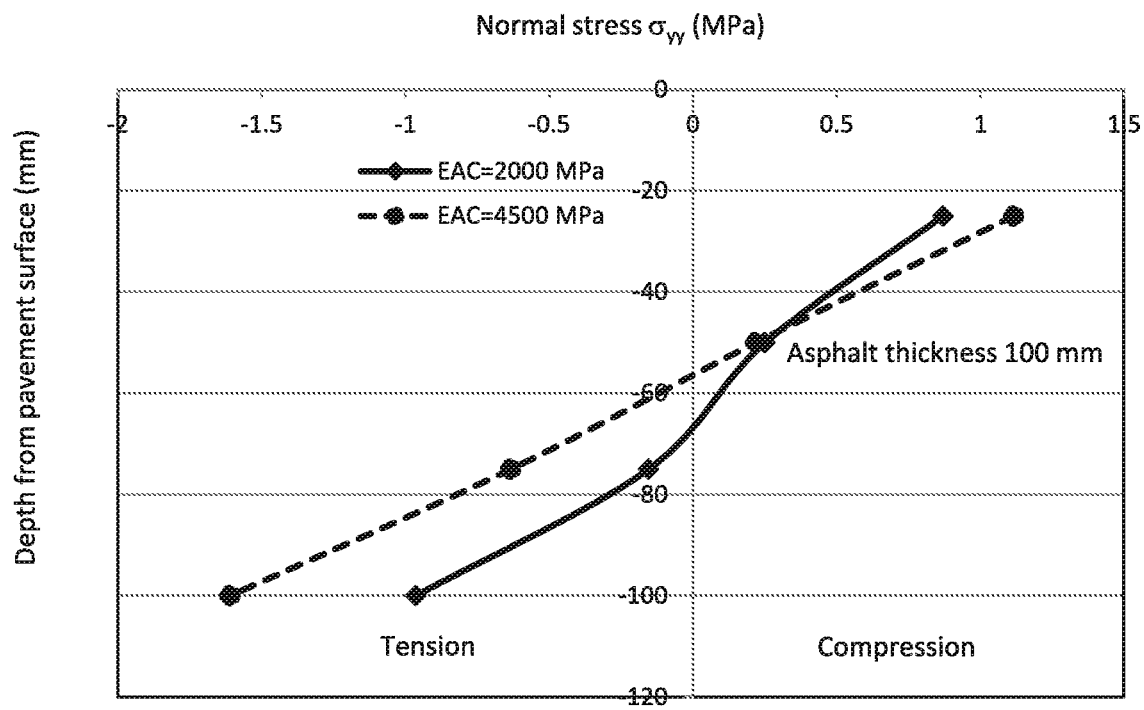
FIG. 6 shows a graph of normal horizontal stresses versus depth for thin asphalt concrete layer (100 mm)
Figure 7:
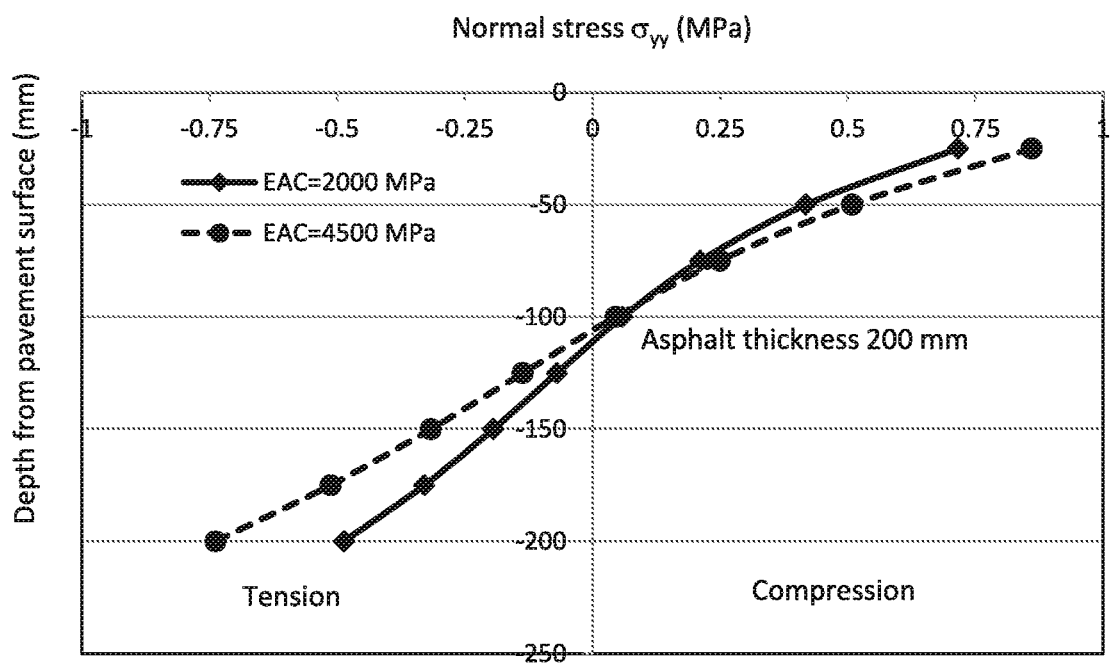
FIG. 7 shows a graph of normal horizontal stresses versus depth for thick asphalt concrete layer (200 mm)

The maximum horizontal normal stresses in both the x direction and the y direction (the direction extending into the page) were determined at different depths as shown in Table 2 and Table 3, and FIG. 6 and FIG. 7. The maximum horizontal normal stresses occur under the outer wheel close to the inner edge of the outer wheel (x=−157 mm from the centre of the dual tyres) in the direction of traffic (y direction). In addition, the maximum horizontal normal stress was recorded at 25 mm depth from the surface for the thin asphalt (100 mm). It was also observed that the higher modulus (4500 MPa) attracts higher horizontal stress of up to 1.116 MPa as shown in Table 2. Therefore, for the wheel tracker test to be representative of field conditions, the Circly simulation suggests that constraining stresses of the asphalt specimen need to be in a similar range of 0.871 to 1.116 MPa as demonstrated in the analysis shown in Table 2 and Table 3, and FIG. 6 and FIG. 7.

In the following section, an estimation of the constraining stresses of several mix types with a wide range of asphalt moduli have been analysed and compared with the Circly computer simulations.

TABLE 2

Circly simulation of normal horizontal stresses under standard axle load for 100 m thick asphalt

| X | Z | E = 2000 MPa, v = 0.4 | | E = 4500 MPa, v = 0.4 | |
| --- | --- | --- | --- | --- | --- |
| (mm) | (mm) | $S_{xx}$ (MPa) | $S_{yy}$ (MPa) | $S_{xx}$ (MPa) | $S_{yy}$ (MPa) |
| 157 | −25 | 0.7857 | 0.871 | 0.9853 | 1.116 |
|  | −50 | 0.2422 | 0.2512 | 0.2133 | 0.2198 |
|  | −75 | −0.25 | −0.153 | −0.5162 | −0.6328 |
|  | −100 | −0.8204 | −0.9634 | −1.361 | −1.609 |

TABLE 3

Circly simulation of normal horizontal stresses under standard axle load for 200 mm thick asphalt

| X | Z | E = 2000 MPa, v = 0.4 | | E = 4500 MPa, V = 0.4 | |
| --- | --- | --- | --- | --- | --- |
| (mm) | (mm) | $S_{xx}$ (MPa) | $S_{yy}$ (MPa) | $S_{xx}$ (MPa) | $S_{yy}$ ( MPa ) |
| 157 | −25 | 0.6562 | 0.7159 | 0.7744 | 0.8603 |
|  | −50 | 0.3848 | 0.4184 | 0.4583 | 0.5088 |
|  | −75 | 0.2003 | 0.2114 | 0.2301 | 0.2493 |
|  | −100 | 0.06815 | 0.0589 | 0.05463 | 0.0451 |
|  | −125 | −0.0411 | −0.0693 | −0.09887 | −0.1362 |
|  | −150 | −0.146 | −0.1939 | −0.2502 | −0.3166 |
|  | −175 | −0.2595 | −0.3294 | −0.4138 | −0.5129 |
|  | −200 | −0.3895 | −0.4866 | −0.6004 | −0.7384 |

Quantifying the Limitations of the Conventional Wheel Tracker Testing Apparatus

Figure 1:
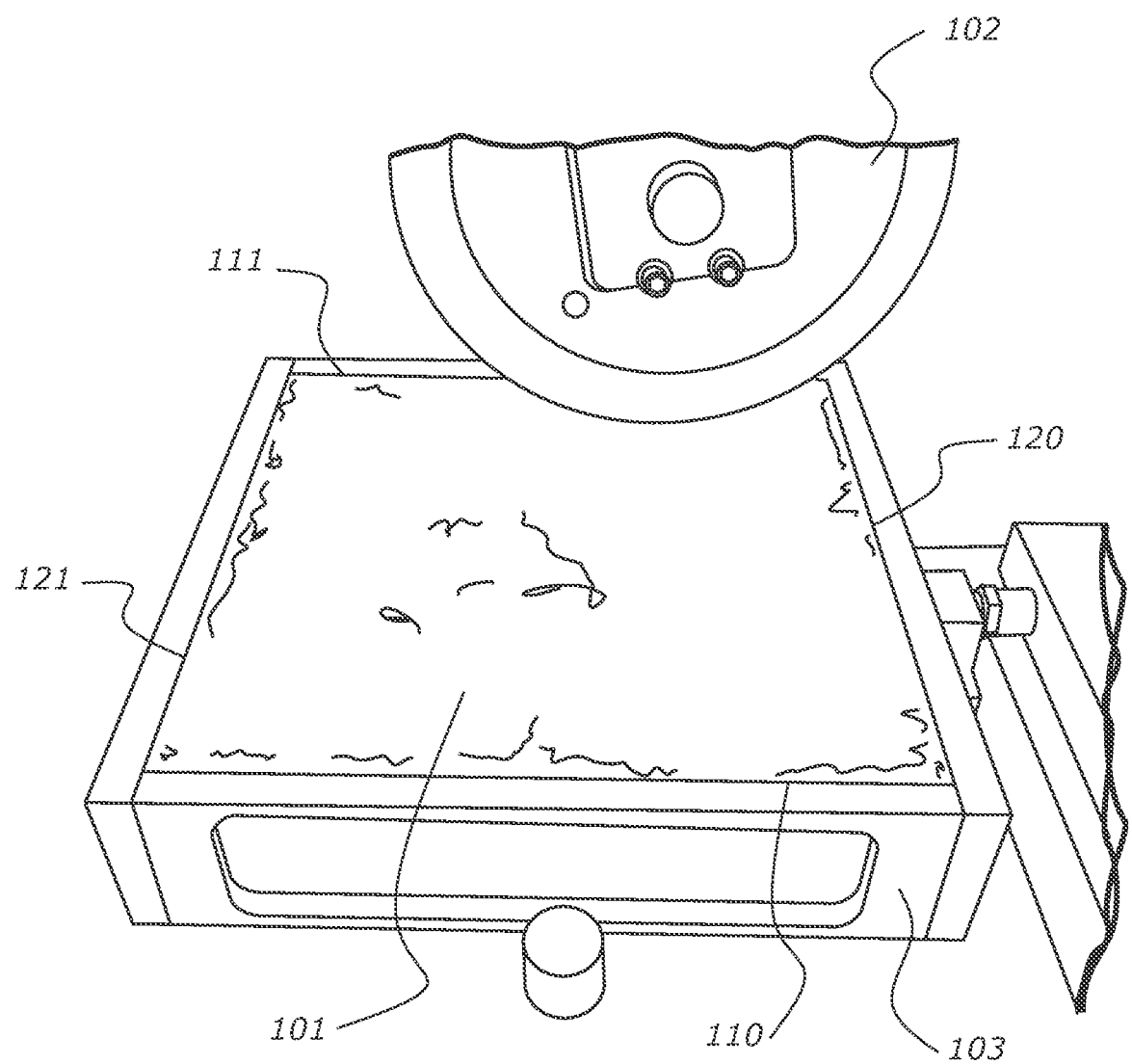
FIG. 1 shows a prior art wheel tracker apparatus.

FIG. 1 illustrates the conventional wheel tracker testing apparatus 100. The asphalt specimen 101 is fully constrained by the specimen holder 103 on all four sides.

In order to quantify the magnitude of the lateral stresses exerted on the specimen in the conventional wheel tracker test, the inventor conducted the partially constrained wheel tracker test of FIG. 2 and FIG. 3 on several types of asphalt mixes of wide range of stiffness moduli including hot mix (HMA), warm mix asphalt (WMA) and warm mix with 25% RAP (25 RAP) and 50% RAP (50 RAP). The specimens were 305 mm×305 mm×75 mm.

Figure 8A:
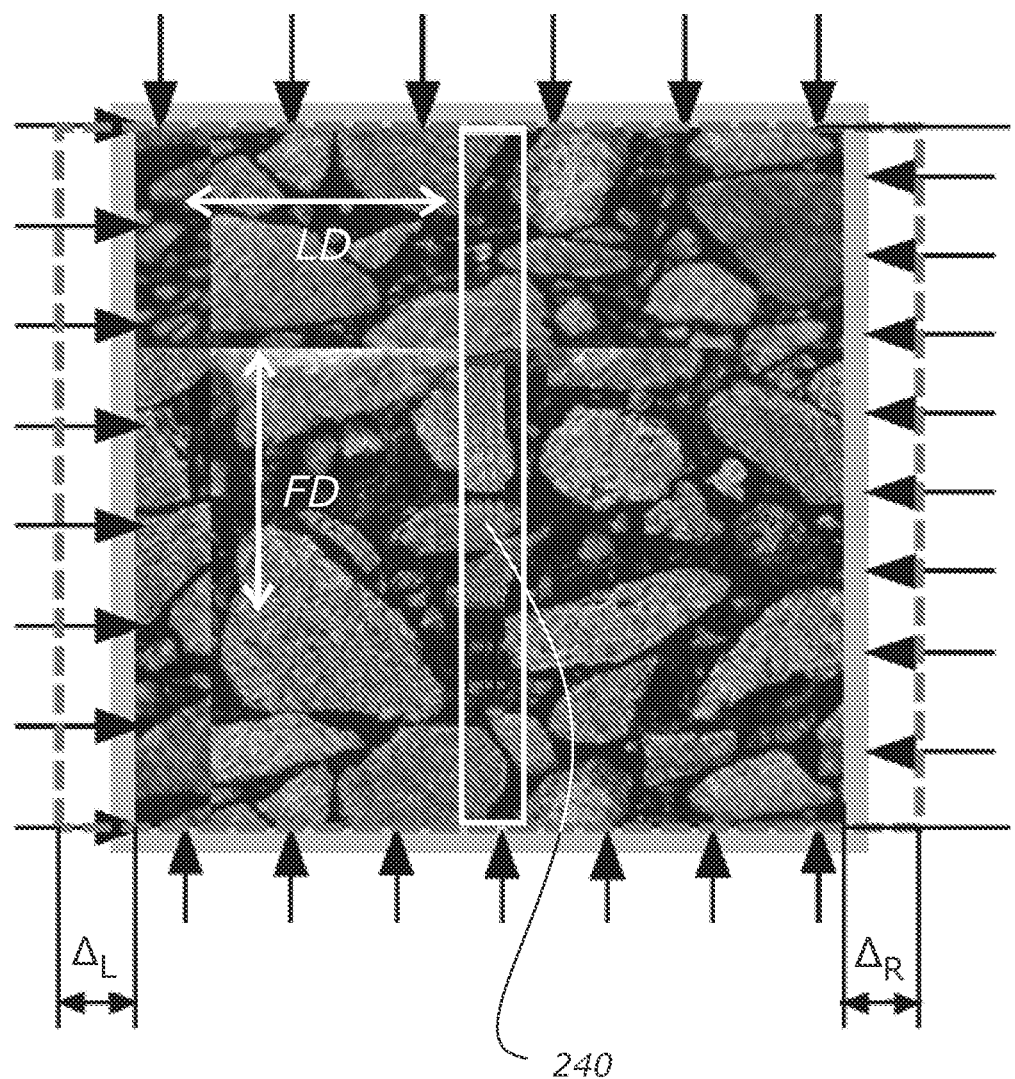
FIG. 8A shows a schematic drawing of the fully constrained test using the apparatus of FIG. 1 superimposed with the partially constrained test of FIGS. 2 and 3.

FIG. 8A shows a schematic drawing of the wheel tracker test with both the constrained test setup of FIG. 1 and the partially constrained test setup of FIG. 2 and FIG. 3 imposed together. In both test setups the wheel follows a wheel tracking path 240. In the partially constrained test setup, both the left and right horizontal deformations ($\Delta_L$ and $\Delta_R$) were recorded as shown in FIG. 2 and FIG. 3.

A dynamic modulus test was carried out using a standard method for the same mixes at different temperatures and frequencies as shown in Table 4.

The wheel tracker testing apparatus speed is 26.4 cycles per minute (0.44 Hz). The dynamic modulus was calculated at 60° C. and 0.44 Hz to represent the specimen modulus during the wheel tracker test.

Table 5 shows the lateral deformation values for thirteen specimens with at least three replicates for four different types of dense graded mixes with wide range of dynamic moduli. The width of the specimen is 305 mm. Therefore, based on the total lateral horizontal deformation ($\Delta_T=(\Delta_L+\Delta_R)$), the average horizontal strain can be computed as shown in Table 5. The horizontal lateral constraining stress can be estimated knowing the dynamic modulus and average horizontal strain as shown in Table 5.

It is apparent that the horizontal constraining stresses applied by the fully constrained specimen holder are quite significant and in the range from 17.3 to 38.76 MPa depending on the stiffness of the mix. Comparing the wheel tracker exerted constraining stresses to the Circly multilayer analysis; it becomes clear that the wheel tracker applies considerably high lateral stresses in the range of 17 to 38 times the expected values. These considerably high lateral constraining stresses will unrealistically boost the permanent deformation resistance of the mixes and limit the ability of the wheel tracker test to produce any valuable information about the effect of mix parameters such as air voids content or binder content on permanent deformation resistance. Therefore, having the specimen fully constrained at all sides will cause the specimen holder to apply large reaction pressure which will severely limit the specimen from lateral (shear) deformation that would have occurred for a similar but partially constrained specimen. Running the wheel tracker test and measuring the deformation in the conventional setup merely indicates measuring rutting caused by densification (i.e. compaction) as a result of air voids change.

TABLE 4

Dynamic modulus and lateral deformation for several dense graded mixes

| Mix type | Frequency (Hz) | Measured Dynamic modulus (MPa) | | | | Avg lateral displacement (rutting test at 60° C.) | | Calculated dynamic modulus (MPa) at 60° C. and 0.44 Hz |
|---|---|---|---|---|---|---|---|---|
| | | 4.4° C. | 21.1° C. | 37.8° C. | 50° C. | Left | Right | |
| HMA | 10 | 15250 | 4652 | 934 | 360 | 17.67 | 18.24 | 146.9 |
| | 5 | 13309 | 3707 | 685 | 261 | | | |
| | 1 | 9560 | 2062 | 366 | 173 | | | |
| | 0.5 | 8225 | 1579 | 297 | 147 | | | |
| | 0.1 | 5537 | 813 | 220 | 131 | | | |
| WMA | 10 | 14733 | 4821 | 866 | 370 | 18.78 | 17.89 | 129.8 |
| | 5 | 12800 | 3832 | 649 | 256 | | | |
| | 1 | 9476 | 2088 | 361 | 162 | | | |
| | 0.5 | 8056 | 1592 | 292 | 129 | | | |
| | 0.1 | 5294 | 846 | 228 | 111 | | | |
| 25RAP | 10 | 18842 | 6353 | 1384 | 523 | 18.70 | 17.84 | 183.8 |
| | 5 | 16072 | 5213 | 1022 | 356 | | | |
| | 1 | 11487 | 3179 | 521 | 225 | | | |
| | 0.5 | 10029 | 2531 | 423 | 188 | | | |
| | 0.1 | 7062 | 1455 | 281 | 155 | | | |
| 50RAP | 10 | 20102 | 8142 | 2200 | 825 | 19.14 | 20.17 | 300.7 |
| | 5 | 17815 | 6785 | 1773 | 622 | | | |
| | 1 | 13539 | 4532 | 1032 | 373 | | | |
| | 0.5 | 12076 | 3768 | 860 | 314 | | | |
| | 0.1 | 9116 | 2361 | 595 | 245 | | | |

TABLE 5

Lateral strain measurements during wheel tracker loading test

| Mix Type | Right Deformation (mm) | Left Deformation (mm) | Horizontal Strain | Average Horizontal Strain | Calculated Average Constraining Stress (MPa) |
|---|---|---|---|---|---|
| HMA 1 | 17.28 | 18.07 | 0.1159 | 0.12 | 17.30 |
| HMA 2 | 15.73 | 17.46 | 0.1088 | | |
| HMA 3 | 18.58 | 18.41 | 0.1213 | | |
| HMA 4 | 19.07 | 19.02 | 0.1249 | | |
| WMA 1 | 17.19 | 17.65 | 0.1142 | 0.12 | 15.61 |
| WMA 2 | 20 | 18.18 | 0.1252 | | |
| WMA 3 | 19.15 | 17.85 | 0.1213 | | |
| 25RAP 1 | 19.11 | 18.34 | 0.1228 | 0.12 | 22.02 |
| 25RAP 2 | 17.42 | 16.15 | 0.1101 | | |
| 25RAP 3 | 19.56 | 19.03 | 0.1265 | | |
| 50RAP 1 | 18.4 | 20.06 | 0.1261 | 0.13 | 38.76 |
| 50RAP 2 | 19.03 | 20.72 | 0.1303 | | |
| 50RAP 3 | 19.99 | 19.73 | 0.1302 | | |

Comparison of Calculated Stress to Actual Stress

The constraining stresses of 17.3 to 38.76 MPa modelled above are likely to be much higher than the actual constraining stresses. This is due to several assumptions made in the analysis. Firstly, the specimen is assumed to remain elastic. This is not the case at 50-60° C., where the specimen will show plastic or viscoplastic behaviour. This is not accounted for in Hooke's law for computing the lateral force. Secondly, the asphalt mix was assumed to be isotropic. However, at 50-60° C. asphalt is anisotropic, with the lateral modulus much smaller than the vertical modulus. It is very difficult to theoretically model the actual material behaviour.

In order to determine the actual constraining stress, the partially constrained test setup of FIG. 2 and FIG. 3 was modified so that the specimen was supported on both ends and one lateral side, and a moveable plate connected to a load cell was positioned adjacent the other lateral side. A dense graded mix (AC14) with 14 mm maximum nominal size, 60/70 binder and 7.0% air voids specimen was tested at 50° C.

Figure 8B:
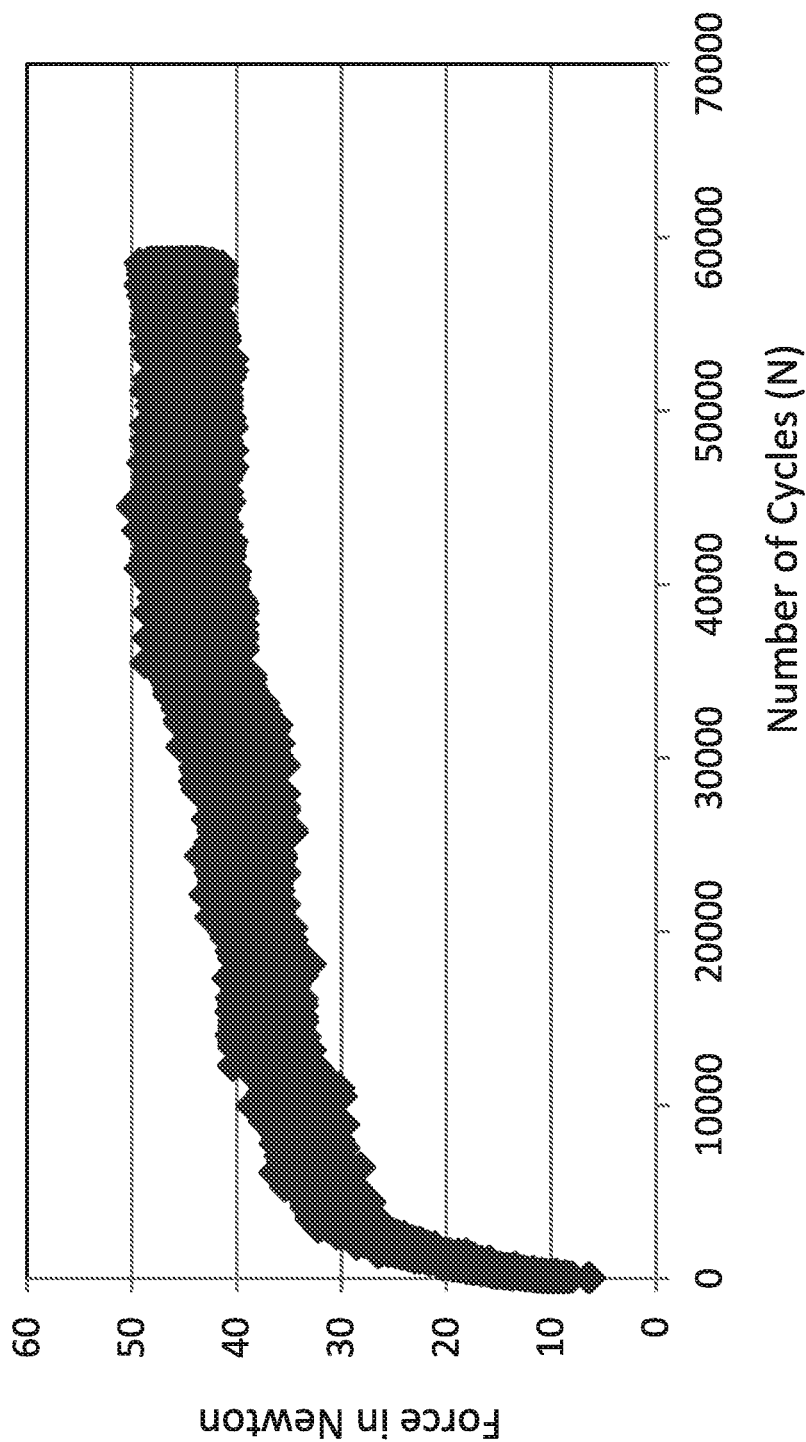
FIG. 8B shows a graph of the measured constraining force in a fully constrained test for an AC14, 60/70 binder, 7.0% air voids specimen tested at 50° C.

FIG. 8B shows the force measured by the load cell during a test. The test starts with the specimen unconstrained (ie the specimen is loosely placed within the specimen holder). As the test progresses, the specimen tries to laterally flow under loading, but is prevented from doing so by the moveable plate constrained by the load cell, and a constraining stress is generated. The constraining stress increases until it reaches an ultimate value which depends on the mix type, binder grade and test temperature.

Figure 10A:
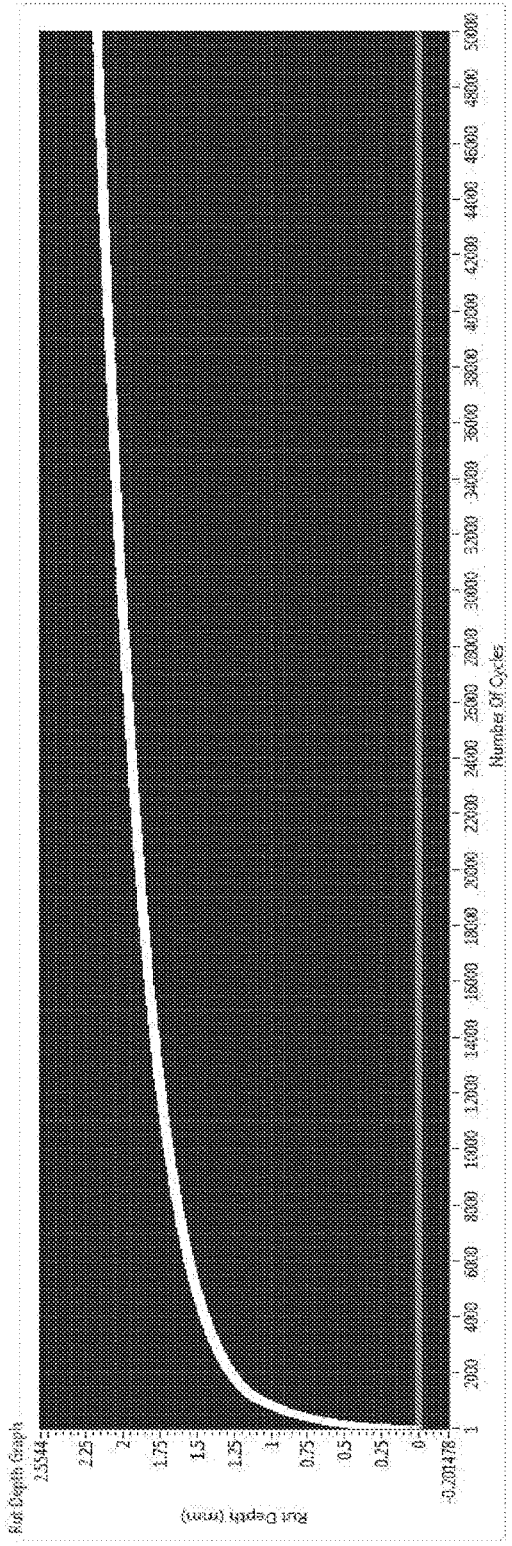
FIG. 10A shows a graph of results from a fully constrained test using the apparatus of FIG. 1—AC20, 60/70 binder, 4.3% air voids, 50° C.

In a conventional fully constrained test, the increase of constraining stresses will result in an artificial increase of the shear strength of the specimen, and increase its resistance to permanent deformation. In a conventional test, tertiary flow is unlikely to be achieved as the permanent deformation curve plateaus as shown in FIGS. 9A and 10A. This explains the very low permanent deformations measured during the conventional fully constrained test and also explains why the majority of specimens tested in the conventional fully constrained test never reach the tertiary flow.

The Effect of the Constraining Stresses on the Permanent Deformation

Figure 10B:
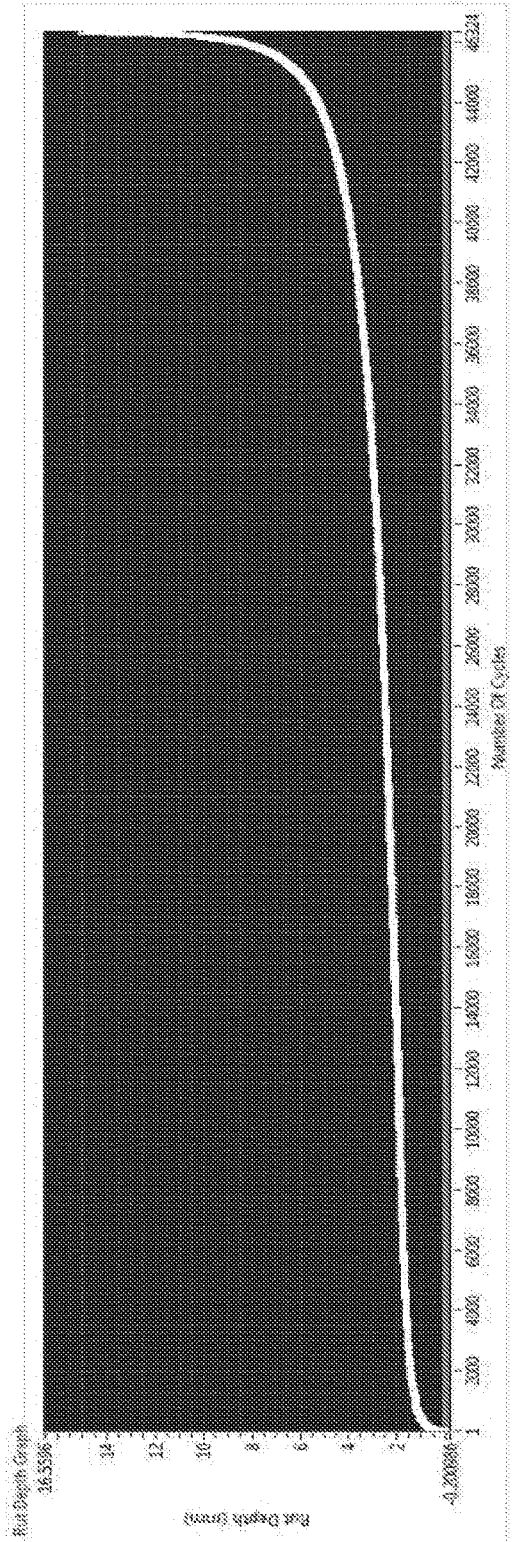
FIG. 10B shows a graph of results from a partially constrained test using the apparatus of FIGS. 2 and 3—AC20, 60/70 binder, 4.3% air voids, 50° C.

FIGS. 9A, 9B, 10A and 10B show the results of the wheel tracker test carried out on two identical pairs of specimens in the fully constrained and the partially constrained setup. All the specimens in FIGS. 9A, 9B, 10A and 10B were made from AC20 mixes. The pair of specimens shown in FIGS. 9A and 9B used soft binder 80/100 penetration grade and air voids content 6.0%. The pair of specimens shown in FIGS. 10A and 10B used a harder binder grade 60/70 and lower air voids content of 4.3%. All specimens were tested at 50° C. FIGS. 9A and 10A show the fully constrained test results for the 80/100 grade specimen and the 60/70 grade specimen respectively. FIGS. 9A and 10A show that the permanent deformation in the fully constrained test plateaus at 2.0 mm regardless of the binder type or air voids content. The fully constrained tests reached 50,000 cycles without the specimens experiencing tertiary failure. FIGS. 9B and 10B show the partially constrained test results for the 80/100 grade specimen and the 60/70 grade specimen respectively. FIGS. 9B and 10B show a significant difference between the two mix types in the partially constrained test. Both specimens experienced tertiary failure in less than 50,000 cycles. The AC20 mix made with the harder 60/70 binder and with 4.3% air voids content lasted nearly 20 times the number of cycles compared to the same AC20 mix with softer 80/100 binder and with higher voids content of 6.0%. This clearly demonstrates that the partially constrained test is more capable of detecting the effect of important mix parameters such as air voids content and binder type on permanent deformation.

As can be seen from the above discussions, the excessive constraining stresses exerted on the asphalt mix by the specimen holder in the conventional wheel tracker test is one of the most important obstacles preventing the true material behaviour. The fully constrained test will most likely be able to capture the small part of the permanent deformation related to the mix densification. However, it is not likely be able to capture the shear related permanent deformations.

Sensitivity to the Mix Volumetric Properties and Test Temperature

In order to investigate the effectiveness of the rut testing apparatus 200 for measuring the effect of different mix volumetric properties and test temperatures, twenty tests with two replicates for each test were conducted. A total of forty specimens with different combinations of aggregate gradations (AC20 and AC14), binder types (60/70 and 80/100) and air voids content (3.5%, 5.5% and 7.0%) were tested at two different temperatures (50° C. and 60° C.) as shown in Table 6. To guarantee capturing a complete deformation curve, the wheel tracker experiment was conducted up to 100,000 cycles or 15 mm vertical deformation, whichever occurred first. The horizontal and vertical deformation and the number of cycles were recorded. Both horizontal and vertical permanent deformation and the number of cycles were modelled by the Francken model given by Equation 1.

$$\delta = AN^B + C(e^{DN} - 1) \quad \text{[Equation 1]}$$

$\delta$ = permanent deformation
N = number of wheel track loading cycles
A, B, C and D = Regression constants depending on the mix properties

TABLE 6

Vertical and horizontal flow number for specimens with different compositions

| T (° C.) | Mix Type | Binder Type | Air Voids % | FN based on vertical deformation ($N_v$) | FN Based on horizontal deformation ($N_h$) |
|---|---|---|---|---|---|
| 50 | AC 20 | 60/70 | 3.5 | No failure | No failure |
|  |  |  | 5.5 | 33805 | 31850 |
|  |  |  | 7.0 | 14660 | 10960 |
|  |  | 80/100 | 3.5 | No failure | No failure |
|  |  |  | 5.5 | 10300 | 7997 |
|  |  |  | 7.0 | 3190 | 2600 |
|  | AC 14 | 60/70 | 3.5 | 14725 | 8900 |
|  |  |  | 5.5 | 9530 | 5340 |
|  |  |  | 7.0 | 8980 | 4600 |
|  |  | 80/100 | 3.5 | 6430 | 3900 |
|  |  |  | 5.5 | 5725 | 3360 |
|  |  |  | 7.0 | 2910 | 1660 |

TABLE 6-continued

Vertical and horizontal flow number for specimens with different compositions

| T (° C.) | Mix Type | Binder Type | Air Voids % | FN based on vertical deformation ($N_v$) | FN Based on horizontal deformation ($N_h$) |
|---|---|---|---|---|---|
| 60 | AC 20 | 60/70 | 3.5 | 17510 | 11110 |
|  |  |  | 5.5 | 4000 | 2200 |
|  |  | 80/100 | 3.5 | 15470 | 9100 |
|  |  |  | 5.5 | 3440 | 2200 |
|  | AC 14 | 60/70 | 3.5 | 5420 | 3600 |
|  |  |  | 5.5 | 1015 | 850 |
|  |  | 80/100 | 3.5 | 3230 | 2300 |
|  |  |  | 5.5 | 840 | 460 |

Figure 11:
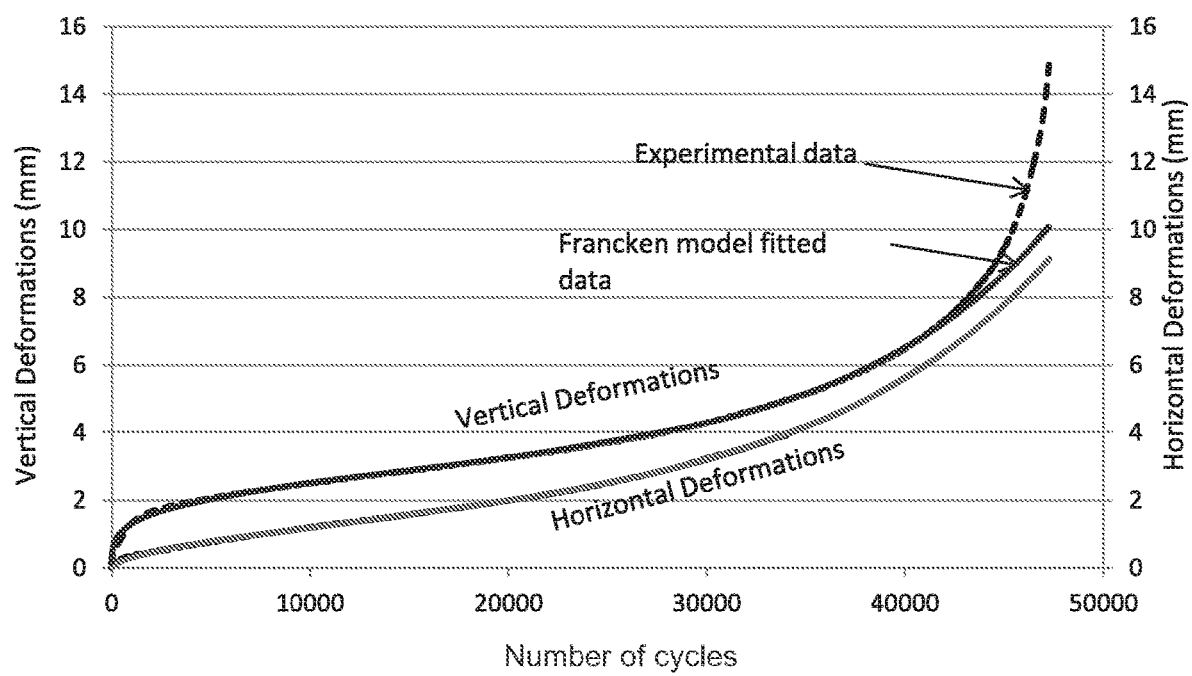
FIG. 11 shows a graph of permanent deformation versus cycle number from a test using the apparatus of FIGS. 2 and 3—AC20, 60/70 binder, 7.0% air voids, 50° C.

FIG. 11 shows the experimental data for the AC20, 60/70 binder, 7.0% air voids, 50° C. specimen displayed as a broken line curve and the Francken model fitted curve represented by solid lines superimposed on the same graph for both vertical and horizontal permanent deformations. The Francken model provided an excellent fit for the experimental data for the three phases of deformation: primary, secondary and tertiary. The rate of change of permanent deformation given by Equation 2 was plotted against the number of cycles as shown in FIGS. 12A to 12G.

$$\frac{d\delta}{dN} = ABN^{B-1} + CDe^{DN} \quad \text{[Equation 2]}$$

FIGS. 12A to 12G show the results of the rate of permanent deformation versus the cycle number for six of the twenty tests conducted utilising the rut testing apparatus 200.

FIGS. 12A to 12G and the data in Table 6 illustrate that by using the partially constrained specimen holder, almost every specimen reaches its failure point, with only very few exceptions. That was not the case for the conventional fully constrained test method. Moreover, unlike the fully constrained approach, the partially constrained wheel tracker test is more sensitive to mix parameters such as air voids content, aggregate gradation, binder type and also to the test temperature. Therefore, ranking the mixtures based on their permanent deformation behaviour becomes more reliable.

Figure 12A:
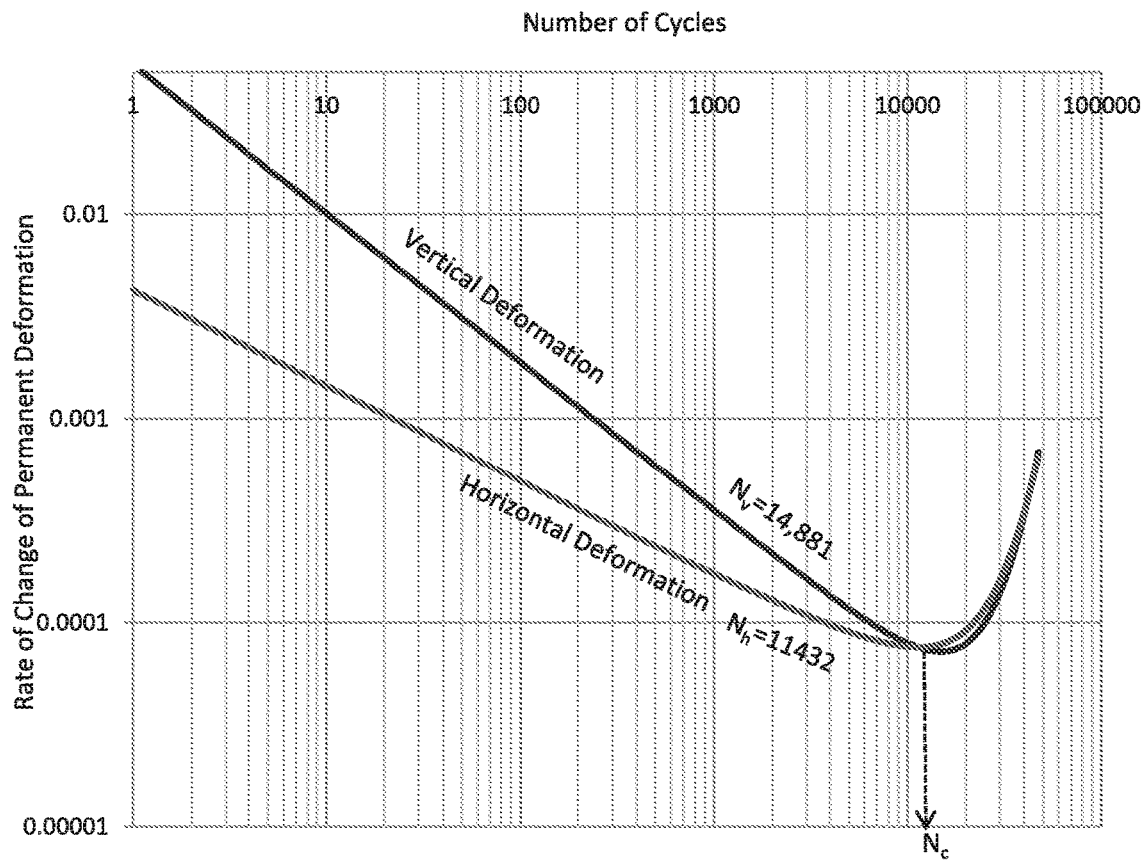
FIG. 12A shows a graph of rate of change of permanent deformation versus cycle number from a test using the apparatus of FIGS. 2 and 3—AC20, 60/70 binder, 7.0% air voids, 50° C.
Figure 12B:
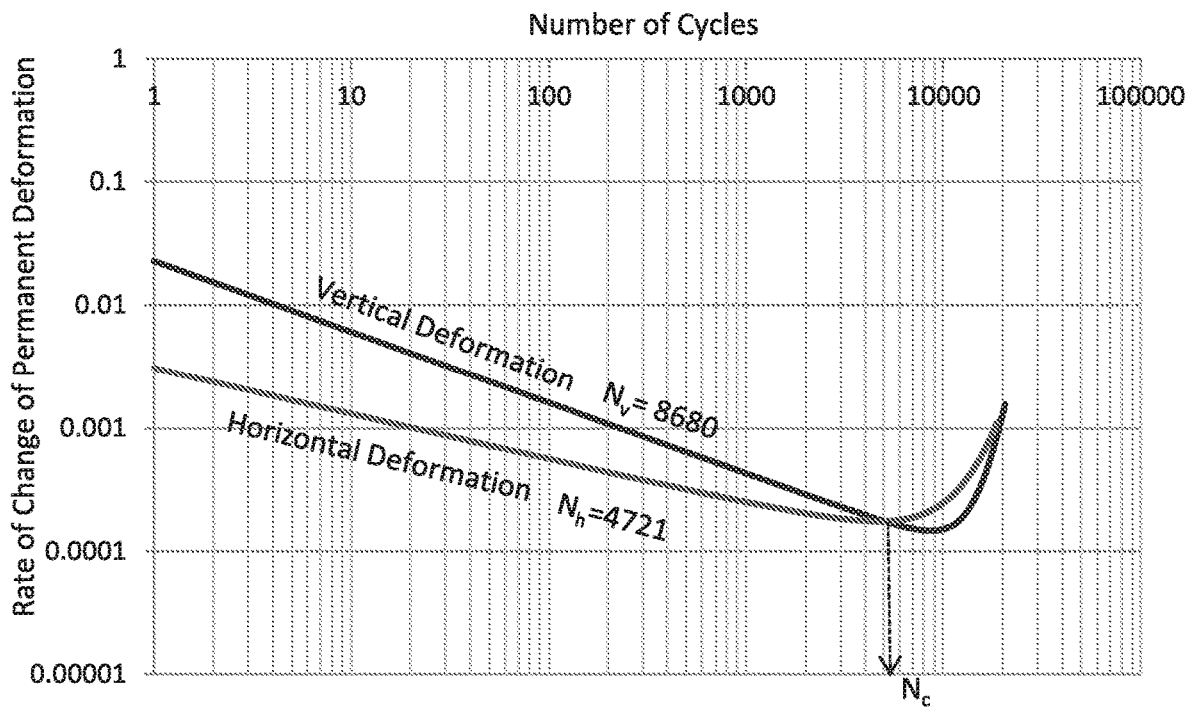
FIG. 12B shows a graph of rate of change of permanent deformation versus cycle number from a test using the apparatus of FIGS. 2 and 3—AC14, 60/70 binder, 7.0% air voids, 50° C.
Figure 12C:
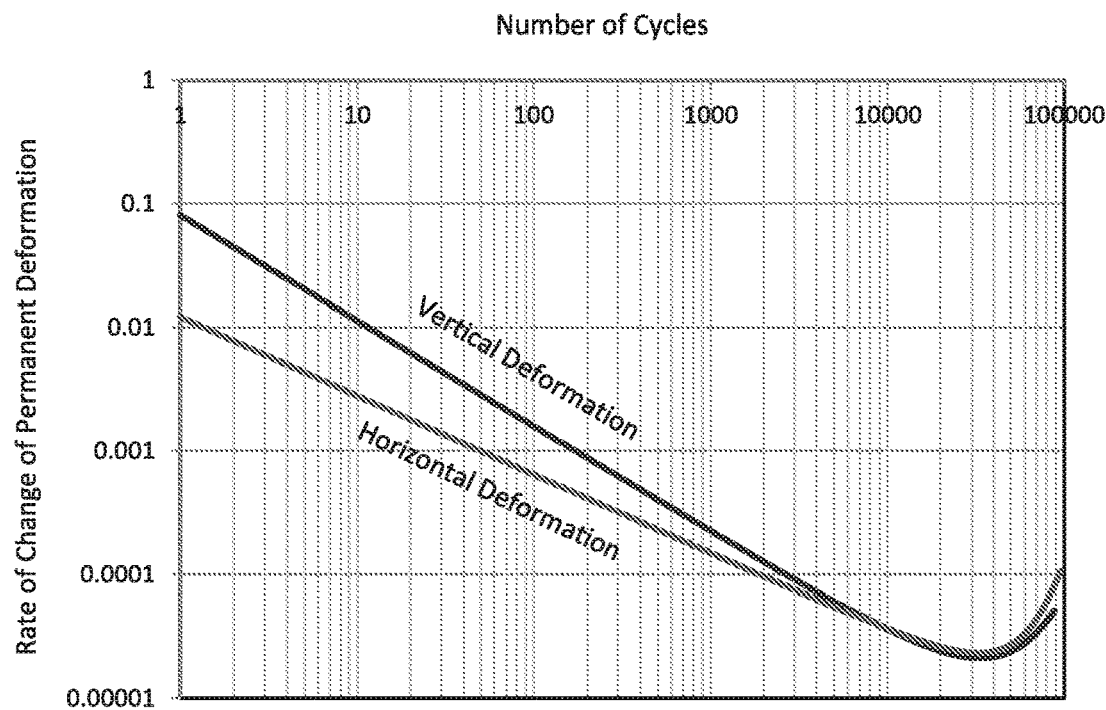
FIG. 12C shows a graph of rate of change of permanent deformation versus cycle number from a test using the apparatus of FIGS. 2 and 3—AC20, 60/70 binder, 5.5% air voids, 50° C.
Figure 12D:
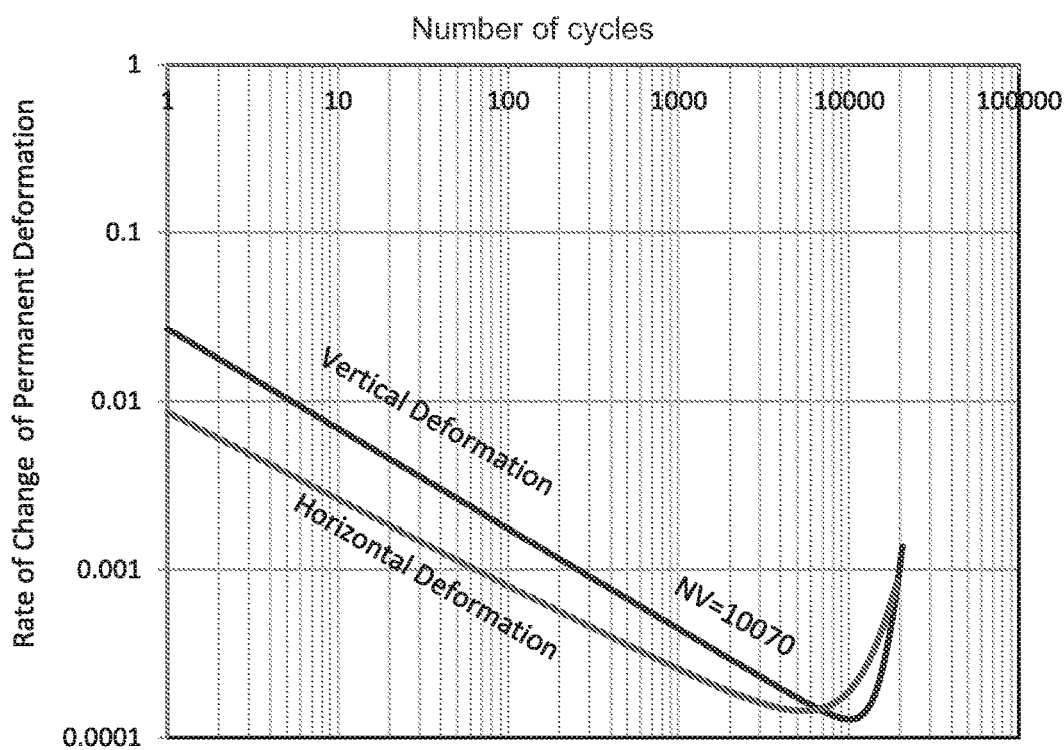
FIG. 12D shows a graph of rate of change of permanent deformation versus cycle number from a test using the apparatus of FIGS. 2 and 3—AC14, 60/70 binder, 5.5% air voids, 50° C.
Figure 12E:
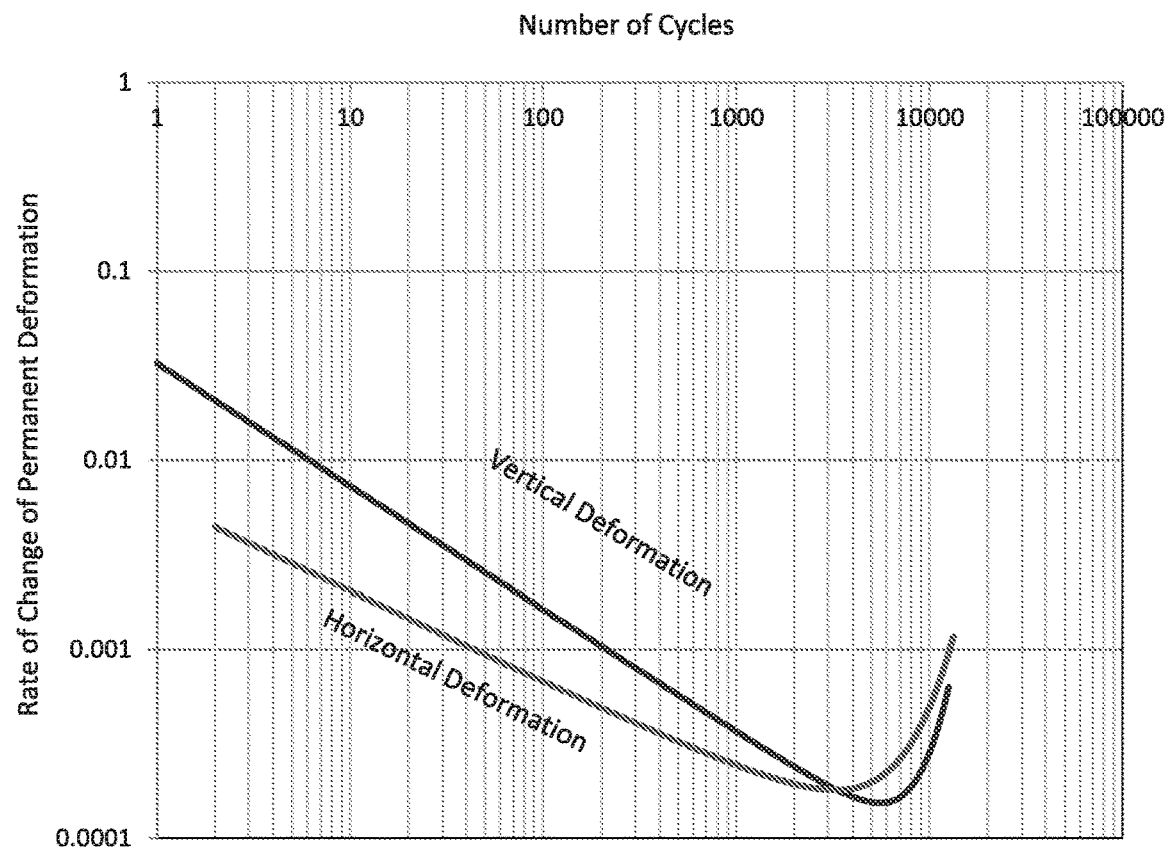
FIG. 12E shows a graph of rate of change of permanent deformation versus cycle number from a test using the apparatus of FIGS. 2 and 3—AC14, 80/100 binder, 5.5% air voids, 50° C.
Figure 12F:
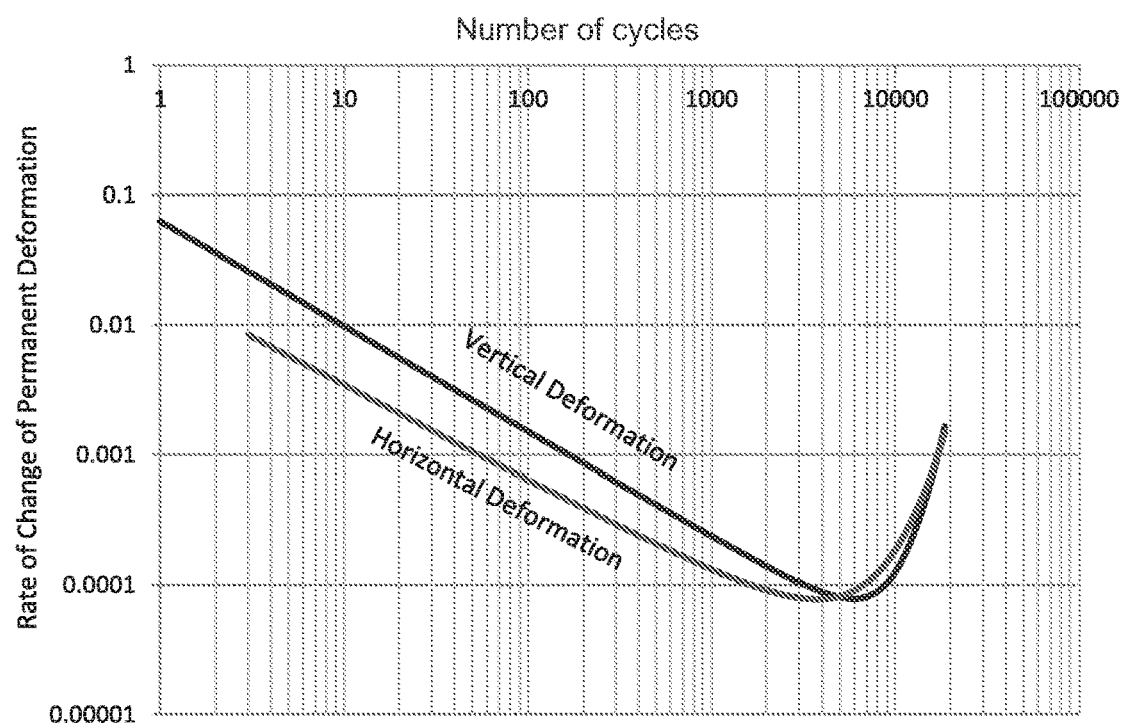
FIG. 12F shows a graph of rate of change of permanent deformation versus cycle number from a test using the apparatus of FIGS. 2 and 3—AC14, 60/70 binder, 3.5% air voids, 60° C.
Figure 12G:
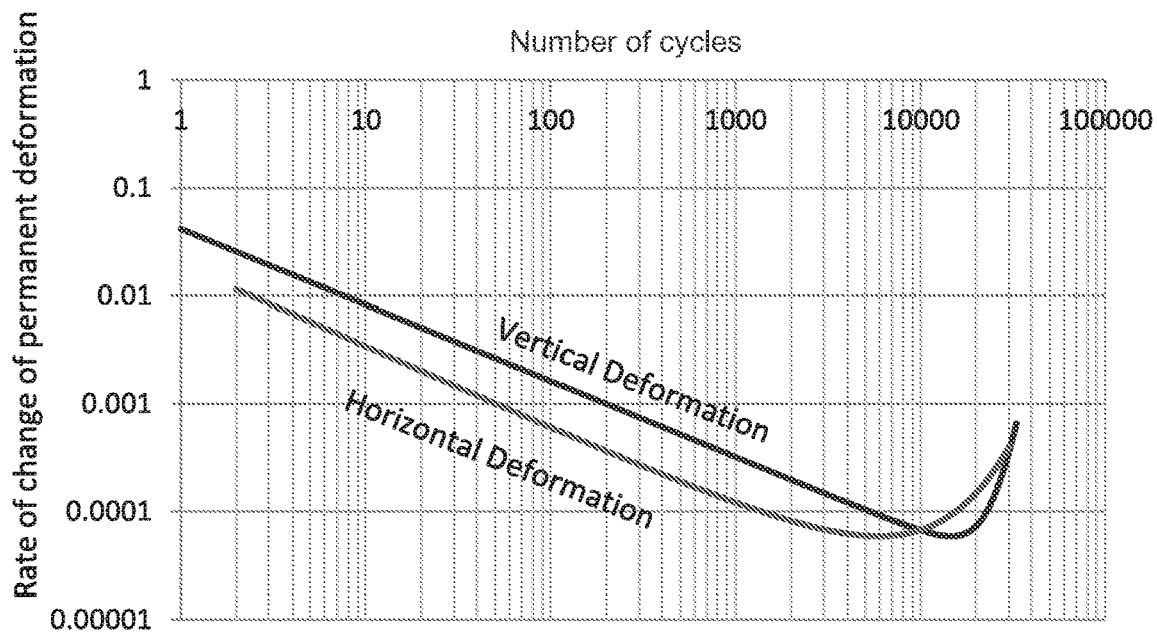
FIG. 12G shows a graph of rate of change of permanent deformation versus cycle number from a test using the apparatus of FIGS. 2 and 3—AC14, 60/70 binder, 3.5% air voids, 50° C.

FIGS. 12A and 12B show the rate of permanent deformation versus the number of cycles for AC20 and AC14, respectively. Both mixes have 60/70 grade bitumen and an air voids content of 7.0%. Both mixes were tested at 50° C. Both horizontal and vertical permanent deformation show the coarse AC20 mix outperforming the medium AC14 mix. In addition, the rate of change of permanent deformation of both horizontal and vertical deformations provides useful information on how the permanent deformation developed in the loaded specimen. The vertical (downward) permanent deformation starts at a higher rate of deformation than the horizontal (lateral) permanent deformation until certain point after which the rate of horizontal permanent deformation overtakes the vertical deformation. The inventor designates this point as the critical flow number ($N_c$) which is defined as the number of cycles at which both vertical and horizontal permanent deformation progress at the same rate. The critical flow number, $N_c$, can be determined as the point of intersection between the rate of vertical permanent deformation curve and the rate of the horizontal permanent deformation curve as shown in FIGS. 12A to 12G.

Before the critical flow number, the mix will densify with rapid change of the air voids content, thus moving faster downward rather than moving laterally. Therefore, the vertical deformation will progress at a faster rate than the horizontal deformation. Beyond the critical flow number, the mix will move laterally at a faster rate with more shear deformation developing in the mix until failure.

Figure 13:
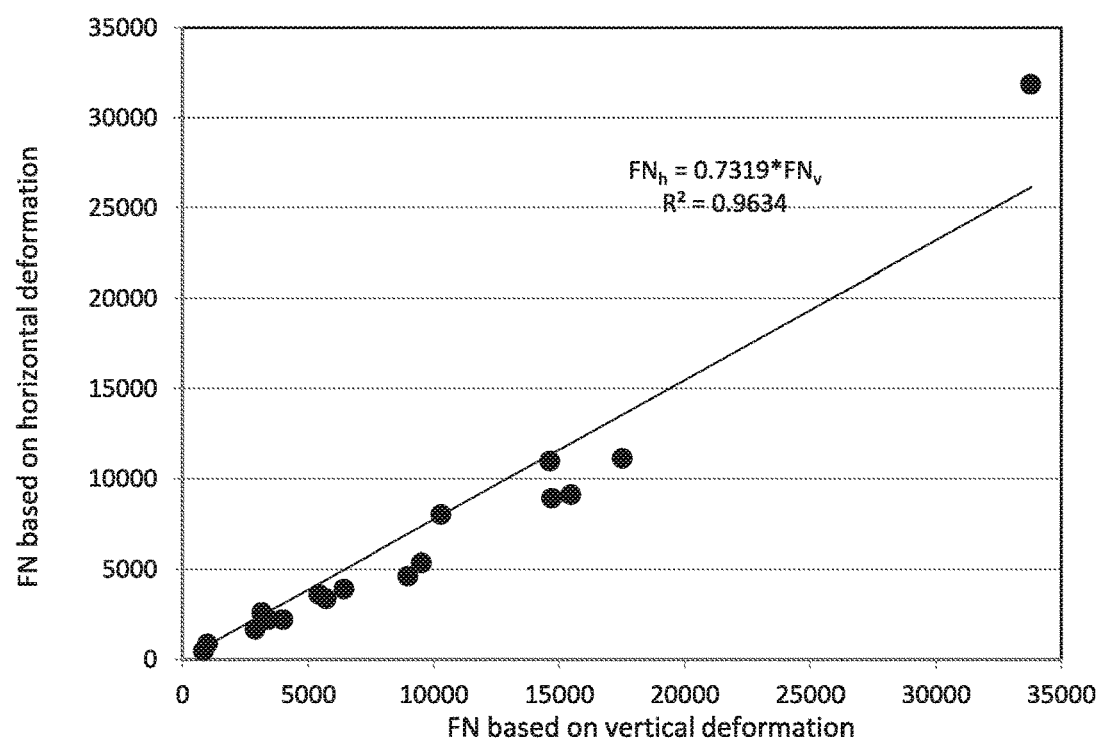
FIG. 13 shows a graph of flow number (FN) based on horizontal deformation versus flow number (FN) based on vertical deformation from a test using the apparatus of FIGS. 2 and 3.

In the tests performed with rut testing apparatus 200, all three zones (primary, secondary, and tertiary zones) of deformation were captured for both vertical (downward) and horizontal (lateral) deformations. The equivalent flow number for the wheel tracker test was calculated using the Francken model as shown in Table 6 [references 13 and 14]. Data shown in Table 6 are the average of two replicates. The point of inflection on the Francken curve was determined as the flow number. The flow number calculated from the vertical (downward) permanent deformation is denoted as $N_v$ and the flow number based on the horizontal (lateral) permanent deformation is denoted as $N_h$. FIG. 13 portrays the relationship between the Flow number based on the horizontal and vertical deformations. The two flow numbers $N_h$ and $N_v$ are well correlated with a coefficient of determination $R^2$ of 0.96. It was also observed that $N_c$ is always larger than $N_h$ and smaller than $N_v$ as shown in FIGS. 12A to 12G (i.e. $N_h<N_c<N_v$). The critical number, $N_c$, can provide useful information regarding the mix lateral stability and therefore its rutting resistance.

As can be seen from the above analysis presented in FIGS. 11 and 12A to 12G and the data in Table 6 above, the partially constrained rut testing apparatus 200 provided a wealth of information to characterize the permanent deformation behaviour of asphalt. In addition, the measured parameters from the vertical (downward) and horizontal (lateral) permanent deformation showed sensitivity to the mix parameters and test temperatures. For example, the change of aggregate gradation from coarse to fine aggregate, i.e. AC20 to AC14, causes the mix to undergo a higher deformation rate. The conclusion also applies to binder grade (hard binder 60/70 to soft binder 80/100), air voids (3.5% to 7.0%) and temperature (50° C. to 60° C.).

Furthermore, by comparing the ratio of the flow numbers based on horizontal to vertical deformations ($N_h/N_v$) for all mixes at different temperature, it was found that this value ranges from as low as 0.51 to as large 0.94. This means that the horizontal deformation can be used in lieu of vertical deformation to shorten the test time by about 5% to 50%. However, it is advantageous to collect both horizontal and vertical deformations as this will provide better understanding and analysis of the permanent deformation behaviour of mixes.

Partially Supported Lateral Side(s)
Moveable Support on One Lateral Side

Figure 14:
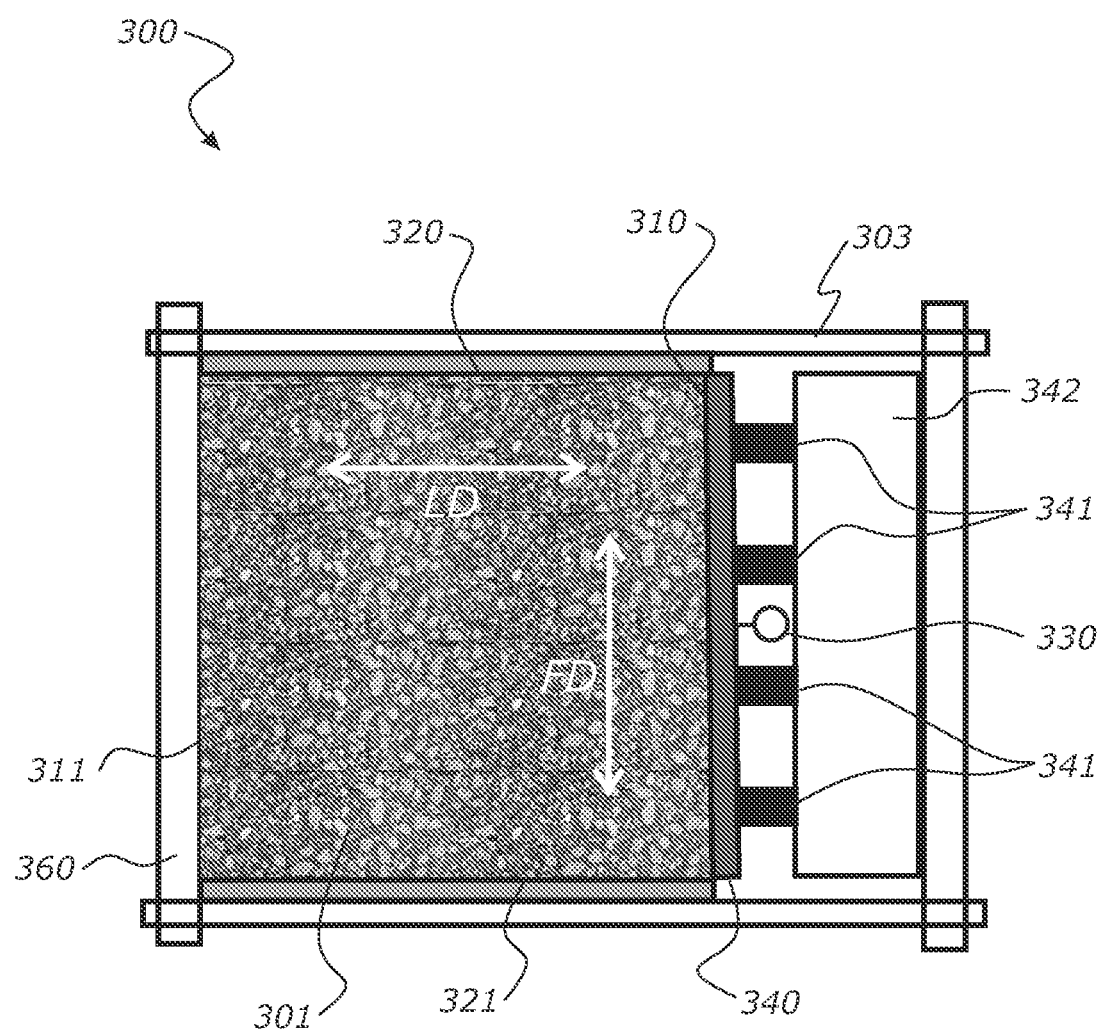
FIG. 14 shows a schematic view of a specimen holder of a second embodiment rut testing apparatus with one lateral moveable support member.

FIG. 14 shows a specimen holder 303 of an alternative embodiment rut testing apparatus for testing the susceptibility of a pavement specimen to rutting. Unless described below, the features and functionality and method of use will be the same as described for the apparatus 200 outlined in relation to FIGS. 2 and 3 above, and like reference numerals indicate like parts with 100 added to each reference numeral.

In this configuration, rather than the lateral sides of the specimen being substantially unsupported, the specimen holder 303 comprises a first moveable support member 340 to support a first lateral side 310 of the specimen 301. The first moveable support member 340 comprises a plate that extends in the first direction FD. The first movable support member 340 is arranged to allow deformation of the specimen 301 in the lateral direction LD.

In an embodiment, the specimen holder 303 is arranged to allow the specimen 301 to deform in the lateral direction LD for substantially the entire test. In an embodiment, the specimen holder 303 is arranged to allow the specimen 301 to deform in the lateral direction LD for the entire test.

A lateral displacement sensor 330 is arranged to determine deformation of the lateral side 310 of the specimen 301 in the lateral direction LD by measuring the movement of support member 340. The sensor comprises a dial test indicator (DTI) or any other suitable linear displacement sensor.

The specimen holder 303 comprises a fixed support member 360 to support a second opposite lateral side 311 of the specimen. The fixed support member 360 is fixed to the base plate and/or end support members in any suitable way.

End support members 320, 321 are fixed.

Figure 16:
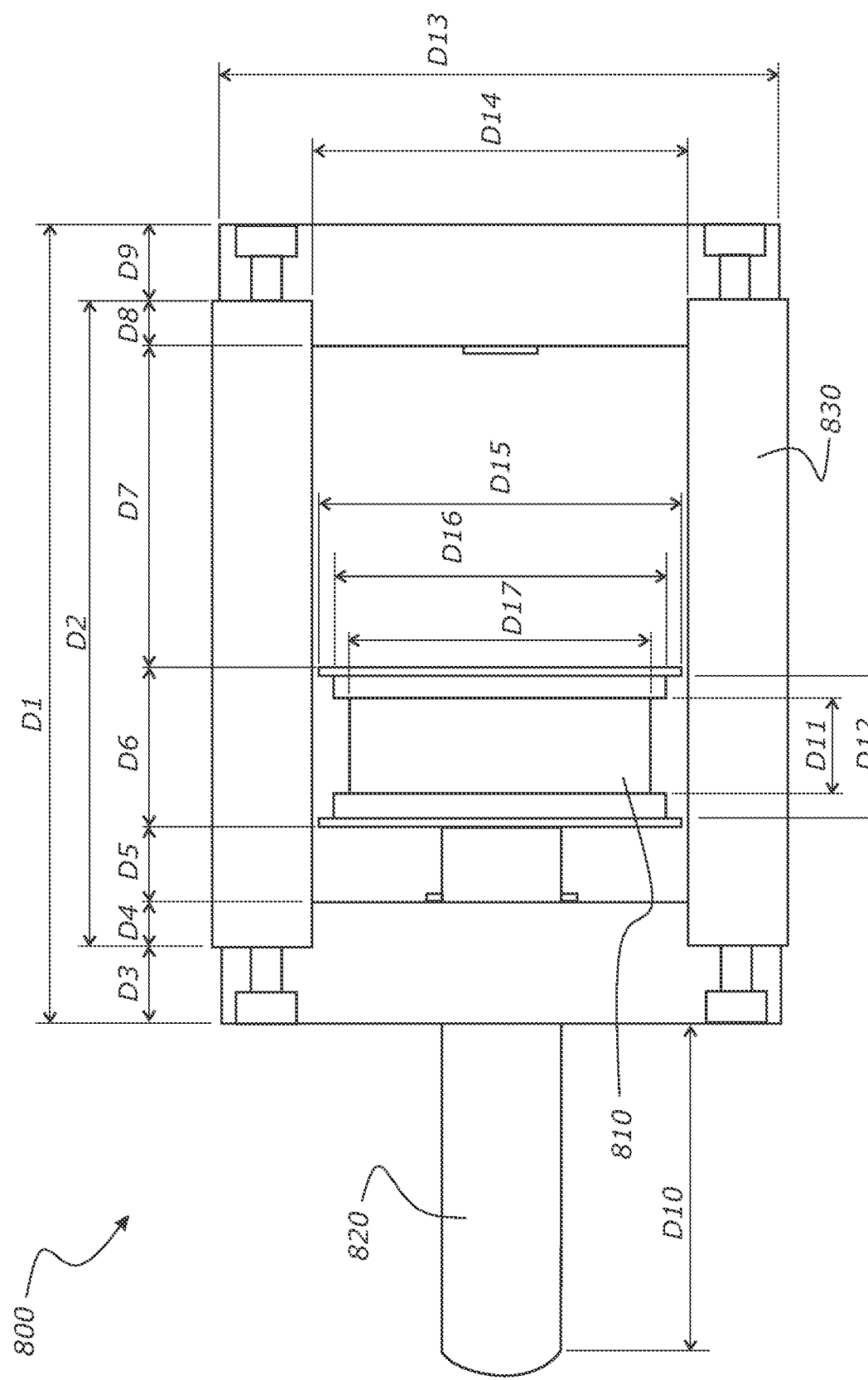
FIG. 16 shows a cross section of an exemplary hydraulic ram for use in the rut testing apparatuses.

The position of the moveable support member 340 is controlled to provide substantially constant pressure to the lateral sides 310, 311 of the specimen during testing. The moveable support member 340 is moved and controlled by hydraulic rams 341 mounted to a hydraulic block 342. An exemplary hydraulic ram is shown in FIG. 16. Pressure is applied by the hydraulic rams 341 to the support member 340. The support member 340 applies pressure on the first side 310 equal to the reaction pressure on the second side 311.

A bleed valve or other suitable mechanism is used to maintain substantially constant pressure during testing. The actual value of the applied lateral pressure can be computed from multilayer computer simulations similar to the analysis in FIGS. 6 and 7 and Table 2. By controlling the lateral pressure, the wheel tracker will provide a better representation of the actual field conditions and therefore better prediction and modelling of the rutting mechanism of the specimen and the material mix.

In an embodiment, the pressure applied by moveable support member 340 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa. In some embodiments, more powerful hydraulic rams are used in order to achieve higher lateral pressure, for example up to 100 kPa to 150 kPa, to suit a wide variety of test conditions.

For some testing applications, the moveable support member 340 could be configured to apply 0 kPa pressure, to simulate an unconstrained side.

A suitable pressure to be applied to a given specimen by the moveable support member 340 may be determined to suit the actual field condition. This pressure will depend on the thickness of the asphalt layer and shoulder support and whether the outer lane or inner lanes are considered. The suitable pressure will be less than the measured constraining stress in a fully constrained specimen.

The applied pressure will also be varied depending on whether test data is required for inner wheel tracks or outer wheel tracks. Typically the outer wheel track is of greater interest as this is generally where the worst damage occurs on an actual road. The outer wheel track generally has lower constraining stresses than the inner wheel track. Therefore, a lower pressure would be applied by the moveable support member 340 to simulate this scenario.

Method

The method of testing the susceptibility of a pavement specimen 301 to rutting is substantially the same as described for apparatus 200 above. The method comprises supporting a first lateral side 310 of the specimen with the first moveable support member 340. The first moveable support member 340 is arranged to allow deformation of the specimen 301 in the lateral direction LD.

The lateral deformation of the lateral side 310 of the specimen 301 is measured with a dial test indicator (DTI) or any other suitable linear displacement sensor arranged to measure the movement of support member 340 in the lateral direction LD.

The method comprises supporting a second opposite lateral side 311 of the specimen with the fixed support member 360.

The method comprises supporting the ends of the specimen with the fixed end support members 320, 321.

The method comprises controlling the position of the moveable support member 340 to provide substantially constant pressure to the sides 310, 311 of the specimen during testing. The moveable support member 340 is moved and controlled by hydraulic rams 341 mounted to a hydraulic block 342. An exemplary hydraulic ram is shown in FIG. 16. Pressure is applied by the hydraulic rams 341 to the support member 340. The support member 340 applies pressure on the first side 310 equal to the reaction pressure on the second side 311.

In an embodiment, the pressure applied by moveable support member 340 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa. In some embodiments, more powerful hydraulic rams are used in order to achieve higher lateral pressure, for example up to 100 kPa to 150 kPa, to suit a wide variety of test conditions. The pressure may be determined as outlined above.

A bleed valve or other suitable mechanism is used to maintain substantially constant pressure during testing.

The apparatus 301 will again suitably be provided with sensors to determine deformation of the specimen in the lateral direction LD and downward deformation of the specimen in the vertical direction. However, this apparatus 301 only uses a single lateral deformation sensor that is operatively coupled to the moveable support member 340.

Moveable Support on Two Lateral Sides

In an alternative embodiment, the specimen second support member 360 may also be a moveable support member, the second moveable support member 360 being arranged to allow deformation of the specimen 301 in the lateral direction LD. This embodiment will suitably comprise a second sensor associated with the second lateral side to determine deformation of the specimen 301 in the lateral direction LD.

In an embodiment, the specimen holder 303 is arranged to allow the specimen 301 to deform in the lateral direction LD for substantially the entire test. In an embodiment, the specimen holder 303 is arranged to allow the specimen 301 to deform in the lateral direction LD for the entire test.

Lateral displacement sensors are arranged to determine deformation of the lateral sides 310 and 311 of the specimen 301 in the lateral direction LD by measuring the movement of support members 340, 360. The sensors comprise dial test indicators (DTIs) or any other suitable linear displacement sensors.

The end support members 320, 321 are fixed.

The position of the moveable support members 340, 360 is controlled to provide substantially constant pressure to the lateral sides 310, 311 of the specimen 301 during testing. The moveable support members 340, 360 are moved and controlled by hydraulic rams mounted to hydraulic blocks. An exemplary hydraulic ram is shown in FIG. 16. Pressure is applied by the hydraulic rams to the support members 340, 360.

In an embodiment, the pressure applied by moveable support members 340, 360 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa. In some embodiments, more powerful hydraulic rams are used in order to achieve higher lateral pressure, for example up to 100 kPa to 150 kPa, to suit a wide variety of test conditions.

For some testing applications, the moveable support members 340, 360 could be configured to apply 0 kPa pressure, to simulate an unconstrained side.

A suitable pressure to be applied to a given specimen by the moveable support members 340, 360 may be determined to suit the actual field condition. This pressure will depend on the thickness of the asphalt layer and shoulder support and whether the outer lane or inner lanes are considered. The suitable pressure will be less than the measured constraining stress in a fully constrained specimen.

A bleed valve or other suitable mechanism is used to maintain substantially constant pressure during testing.

Method

The method of testing the susceptibility of a pavement specimen 301 to rutting is substantially the same as described for apparatus 300 above. The method comprises supporting a second opposite lateral side 311 of the specimen with the second moveable support member 360, wherein the second moveable support member is arranged to allow deformation of the specimen 301 in the lateral direction LD.

The lateral deformation of the lateral sides 310, 311 of the specimen 301 is measured with dial test indicators (DTIs) or any other suitable linear displacement sensors arranged to measure the movement of support members 340, 360 in the lateral direction LD.

The method comprises controlling the position of the moveable support members to provide substantially constant pressure to the sides 310, 311 of the specimen 301 during testing. The moveable support members 340, 360 are moved and controlled by hydraulic rams mounted to hydraulic blocks. An exemplary hydraulic ram is shown in FIG. 16. Pressure is applied by the hydraulic rams to the support members 340, 360.

In an embodiment, the pressure applied by moveable support members 340, 360 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa.

In some embodiments, more powerful hydraulic rams are used in order to achieve higher lateral pressure, for example up to 100 kPa to 150 kPa, to suit a wide variety of test conditions. The pressure may be determined as outlined above.

A bleed valve or other suitable mechanism is used to maintain substantially constant pressure during testing.

Partially Supported Lateral Sides and Ends

Moveable Support on One Lateral Side and One End

Figure 15:
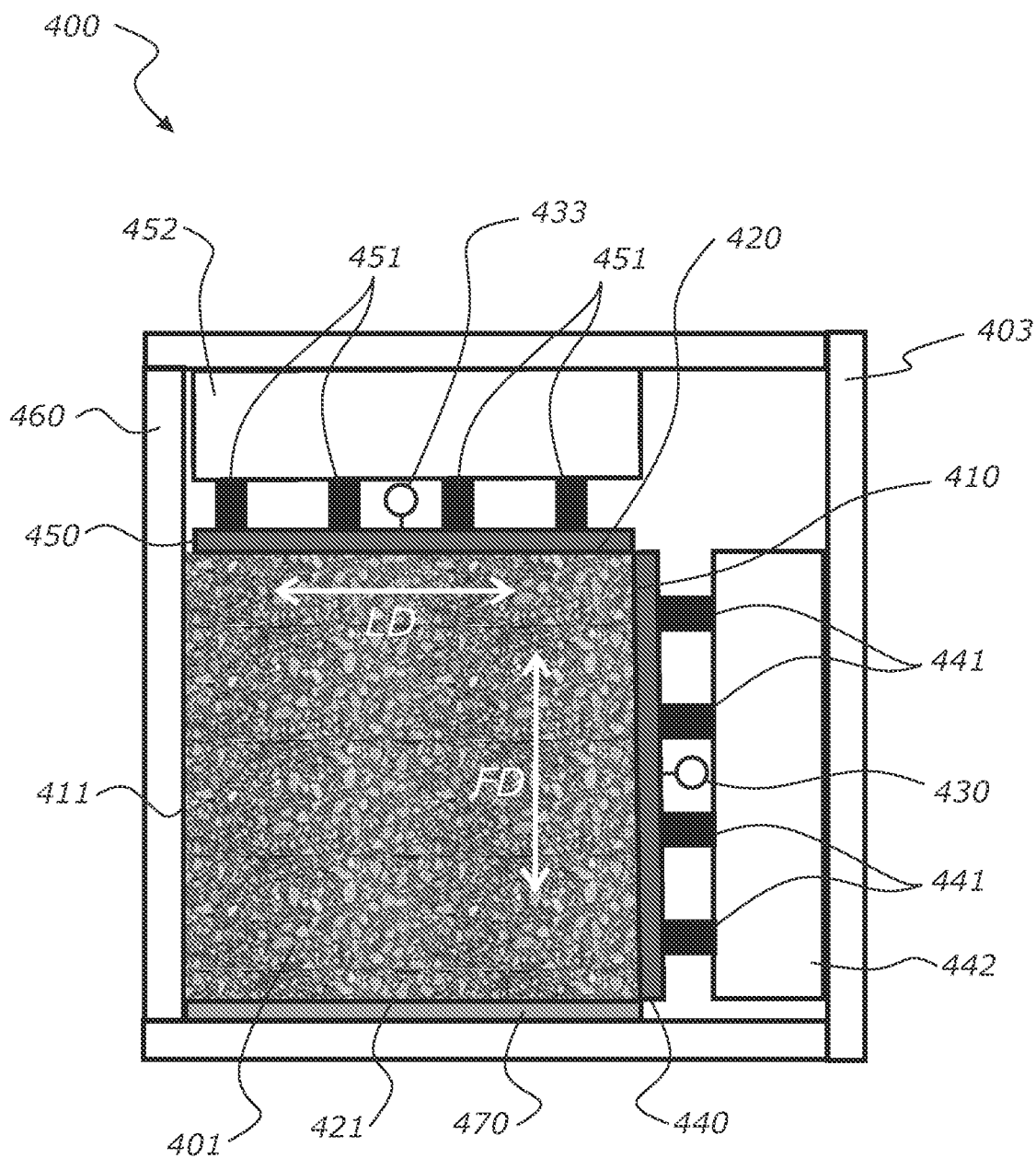
FIG. 15 shows a schematic view of a specimen holder of a third embodiment rut testing apparatus with one lateral moveable support member and one end moveable support member.

FIG. 15 shows a specimen holder 403 of an alternative embodiment rut testing apparatus for testing the susceptibility of a pavement specimen to rutting. Unless described below, the features and functionality and method of use will be the same as described for the apparatus 200 outlined in relation to FIGS. 2 and 3 above, and like reference numerals indicate like parts with 200 added to each reference numeral.

The specimen holder 403 comprises a first moveable support member 440 to support a first lateral side 410 of the specimen 401 and a first end moveable support member 450 to support a first end 420 of the specimen. The first movable support member 440 is arranged to allow deformation of the specimen 401 in the lateral direction LD and the first end moveable support member 450 is arranged to allow deformation of the specimen 401 in the first direction FD that extends between the opposite ends 420, 421 of the specimen.

In an embodiment, the specimen holder 403 is arranged to allow the specimen 401 to deform in the lateral direction LD and the first direction FD for substantially the entire test. In an embodiment, the specimen holder 403 is arranged to allow the specimen 401 to deform in the lateral direction LD and the first direction FD for the entire test.

The specimen holder 403 comprises fixed support members 460, 470 to support a second opposite lateral side 411 of the specimen 401 and a second opposite end 421 of the specimen 401.

The position of the moveable support members 440, 450 is controlled to provide substantially constant pressure in the range of 300 to 350 kPa to the sides 410, 411 and ends 420, 421 of the specimen 401 during testing. The moveable support members 440, 450 are moved and controlled by hydraulic rams 441, 451 mounted to hydraulic blocks 442, 452. An exemplary hydraulic ram is shown in FIG. 16. Pressure is applied by the hydraulic rams 441, 451 to the support members 440, 450. The support member 440 applies pressure on the first side 410 equal to the reaction pressure on the second side 411. The support member 450 applies pressure on the first end 420 equal to the reaction pressure on the second end 421.

In an embodiment, the pressure applied by moveable support members 440, 450 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa. In some embodiments, more powerful hydraulic rams are used in order to achieve higher pressure, for example up to 100 kPa to 150 kPa, to suit a wide variety of test conditions.

In some embodiments, greater pressure is applied by the end support member 450 than by the side support member 440.

For some testing applications, the side support member 440 could be configured to apply 0 kPa pressure to simulate an unconstrained side.

A suitable pressure to be applied to a given specimen by the first moveable support member 440 may be determined to suit the actual field condition. This pressure will depend on the thickness of the asphalt layer and shoulder support and whether the outer lane or inner lanes are considered. The suitable pressure will be less than the measured constraining stress in a fully constrained specimen.

In an embodiment, an end displacement sensor 433 is arranged to determine deformation of the end 420 of the specimen 401 in the first direction FD that extends between the opposite ends by measuring the movement of support member 450. The sensor comprises a dial test indicator (DTI) or any other suitable linear displacement sensor. Two flow numbers, $N_{h1}$ and $N_{h2}$ can be determined, one for horizontal displacement in each direction FD, LD. Both of these flow numbers $N_{h1}$ and $N_{h2}$ could be used, or the average of the flow numbers $N_{h1}$ and $N_{h2}$ could be used, in the method and apparatus of embodiments of the invention.

The hydraulic rams 441 on the first lateral side support member 440 and the hydraulic rams 451 on the first end support member 450 may be configured or controlled to apply different pressures. In some embodiments the pressure applied to the lateral sides 410, 411 is the same as the pressure applied to the ends 420, 421. In other embodiments the pressure applied to the lateral sides 410, 411 is different to the pressure applied to the ends 420, 421.

A bleed valve or other suitable mechanism is used to maintain substantially constant pressure during testing.

It is believed that embodiments comprising moveable support members on at least one lateral side and at least one end will be a better match for field conditions than embodiments with moveable support member(s) only in the lateral direction. As the embodiments with a moveable support member on at least one end will more accurately simulate the stresses in an actual pavement, they will provide a better prediction of permanent deformation. This test data can be used in modelling to predict material behaviour.

It is also believed that applying different pressures on the sides 410, 411 and ends 420, 421 will better represent field conditions for some asphalt mixes.

Method

The method of testing the susceptibility of a pavement specimen 401 to rutting is substantially the same as described for apparatus 200 above. The method comprises supporting the first lateral side 410 of the specimen 401 with the first moveable support member 440 and supporting a first end 420 of the specimen 401 with the first end moveable support member 450. The first movable support member 440 is arranged to allow deformation of the specimen 401 in the lateral direction LD and the first end moveable support member 450 is arranged to allow deformation of the specimen 401 in the first direction FD that extends between the opposite ends 420, 421 of the specimen.

The method comprises supporting a second opposite lateral side 411 of the specimen 401 and a second opposite end 421 of the specimen with the fixed support members 460, 470.

The method comprises controlling the position of the moveable support members 440, 450 to provide substantially constant pressure to the sides 410, 411 and ends 420, 421 of the specimen 401 during testing. The moveable support members 440, 450 are moved and controlled by hydraulic rams 441, 451 mounted to hydraulic blocks 442, 452. An exemplary hydraulic ram is shown in FIG. 16. Pressure is applied by the hydraulic rams 441, 451 to the support members 440, 450. The support member 440 applies pressure on the first side 410 equal to the reaction pressure on the second side 411. The support member 450 applies pressure on the first end 420 equal to the reaction pressure on the second end 421.

In an embodiment, the pressure applied by moveable support members 440, 450 is greater than 0 kPa and up to 150 kPa. In some embodiments, the pressure is in the range of 10 kPa to 150 kPa. In some embodiments, the pressure is in the range of 10 kPa to 30 kPa. In some embodiments, the pressure is in the range of 20 kPa to 30 kPa. In some embodiments, more powerful hydraulic rams are used in order to achieve higher pressure, for example up to 100 kPa to 150 kPa, to suit a wide variety of test conditions. The pressure may be determined as outlined above.

In an embodiment, the deformation of the end 420 of the specimen 401 is measured with a dial test indicator (DTI) or any other suitable linear displacement sensor arranged to measure the movement of support member 450 in the first direction FD that extends between the opposite ends. Two flow numbers, $M_{h1}$ and $N_{h2}$ can be determined, one for horizontal displacement in each direction FD, LD. Both of these flow numbers $M_{h1}$ and $N_{h2}$ could be used, or the average of the flow numbers $M_{h1}$ and $N_{h2}$ could be used, in the method and apparatus of embodiments of the invention. The average of $M_{h1}$ and $N_{h2}$ could be used to determine the resistance to lateral deformation.

The hydraulic rams 441 on the first lateral side support member 440 and the hydraulic rams 451 on the first end support member 450 may be configured or controlled to apply different pressures. In some embodiments the pressure applied to the lateral sides 410, 411 is the same as the pressure applied to the ends 420, 421. In other embodiments the pressure applied to the lateral sides 410, 411 is different to the pressure applied to the ends 420, 421.

A bleed valve or other suitable mechanism is used to maintain substantially constant pressure during testing.

It is understood that embodiments comprising moveable support members on at least one lateral side and at least one end will be a better match for field conditions than embodiments with moveable support member(s) only in the lateral direction. It is also understood that applying different pressures on the sides 410, 411 and ends 420, 421 better represents field conditions for some asphalt mixes.

Moveable Support on Two Lateral Sides and Two Ends

In an alternative embodiment, the second support member 460 to support a second lateral side 411 of the specimen 401 is a moveable support member and the second end support member 470 to support a second end 421 of the specimen 401 is a moveable support member. The moveable support members 460 and 470 will be supported and controlled in the same way described above for the support members 410, 420. The second movable support member 460 is arranged to allow deformation of the specimen 401 in the lateral direction LD and the second end moveable support member 470 is arranged to allow deformation of the specimen 401 in the first direction FD that extends between the opposite ends of the specimen 420, 421.

In an embodiment, the specimen holder 403 is arranged to allow the specimen 401 to deform in the lateral direction LD and the first direction FD for substantially the entire test. In an embodiment, the specimen holder 403 is arranged to allow the specimen 401 to deform in the lateral direction LD and the first direction FD for the entire test.

This embodiment comprises a second sensor associated with the second lateral side 411 to determine deformation of the specimen 401 in the lateral direction LD.

An alternative embodiment further comprises end displacement sensors associated with ends 420, 421 to determine deformation of the specimen 401 in the first direction FD that extends between the opposite ends. Two flow numbers, $M_{h1}$ and $N_{h2}$ can be determined, one for horizontal displacement in each direction FD, LD. $M_{h1}$ can be determined based on the average deformation in the LD direction, and $N_{h2}$ can be determined based on the average deformation in the FD direction. Both of these flow numbers $M_{h1}$ and $N_{h2}$ could be used, or the average of the flow numbers $M_{h1}$ and $N_{h2}$ could be used, in the method and apparatus of embodiments of the invention.

A suitable pressure to be applied to a given specimen by the second moveable support member 460 and the second end moveable support member 470 may be determined to suit the actual field condition. This pressure will depend on the thickness of the asphalt layer and shoulder support and whether the outer lane or inner lanes are considered. The suitable pressure will be less than the measured constraining stress in a fully constrained specimen. The pressure may be in the ranges outlined above.

Method

The method of testing the susceptibility of a pavement specimen (401) to rutting is substantially the same as described for apparatus 400 above. The method comprises supporting a second lateral side 411 of the specimen 401 with the second moveable support member 460 and supporting a second opposite end 421 of the specimen with the second end moveable support member 450. The second movable support member is arranged to allow deformation of the specimen 401 in the lateral direction LD and the second end moveable support member is arranged to allow deformation of the specimen 401 in the first direction FD that extends between the opposite ends 420, 421 of the specimen.

The method comprises controlling the position of the moveable support members 410, 420, 460, 470 to provide substantially constant pressure to the sides 410, 411 and ends 420, 421 of the specimen 401 during testing. The pressure may be determined as outlined above.

Other Configurations

Other configurations of moveable and fixed supports are possible, such as moveable support on two lateral sides and one end, and a fixed support on the other end. An alternative configuration is moveable support on one lateral side and two ends, and a fixed support on the other lateral side.

Hydraulic Rams

An exemplary hydraulic ram 800 suitable for use in any of the above embodiments is shown in FIG. 16. The ram 800 comprises a piston 810 attached to a shaft 820. The piston is moveable within a housing 830. The ram also has a bleed valve to control the pressure that is applied by the ram, and thereby the pressure that is applied by the respective moveable support member to the specimen during testing. The bleed valve will be controllable to set the desired pressure.

Exemplary dimensions are:
D1=106 mm
D2=86 mm
D3=10 mm
D4=6 mm
D5=10 mm
D6=21 mm
D7=43 mm
D8=6 mm
D9=10 mm
D10=43 mm
D11=11 mm
D12=19 mm
D13=74 mm
D14=50 mm
D15=49.5 mm
D16=46 mm
D17=40 mm.

Preferred embodiments of the invention have been described by way of example only and modifications may be made thereto without departing from the scope of the invention.

For example, the specimen, and specimen holder, may be any suitable shape, such as square, rectangular, circular, or any other suitable shape.

Reference herein may be used to directional terminology such as 'vertical', 'downward' etc. Those terms are intended in a relative sense compared to other directions, and are representative of use of the apparatus with the specimen holder in a horizontal orientation and with the wheel apply-

REFERENCES

1. Archilla, Adrian Ricardo, & Madanat, Samer. (2000). Development of a pavement rutting model from experimental data. Journal of Transportation Engineering, 126 (4), 291-299. doi: 10.1061/(asce)0733-947x(2000)126:4 (291)
2. Witczak, M. W. (2007). Specification Criteria for Simple Performance Tests for Rutting Volume I: Dynamic Modulus (E*) Volume II: Flow Number and Flow Time. WASHINGTON, D.C.
3. Witczak, M. W., Kaloush, K., Pellinen, T., El-Basyouny, M., & Von Quintus, H. (2002). Simple Performance Test for Superpave Mix Design. Washington, D.C.
4. Witczak, M. W. (2005). Simple Performance Tests: Summary of Recommended Methods and Database. Washington, D.C.: Transportation Research Board.
5. Kandhal, P. S., and Cooley, L. A. (2003). Accelerated Laboratory Rutting tests: Evaluation of the Asphalt Pavement Analyzer. Washington D.C.
6. Ahmad, J., Abdul Rahman, M, Y., and Hainin, M., R. (2011). Rutting Evaluation of Dense Graded Hot Mix Asphalt Mixture. International Journal of Engineering & Technology 11(05).
7. Lu, Q., and Harvey, J. T. (2006). Evaluation of Hamburg Wheel-Tracking Device Test with Laboratory and Field Performance Data. Transportation Research Record: Journal of the Transportation Research Board.
8. Australian Standard. (2005). Commentary to AG:PT/T220—Sample Preparation—Compaction of Asphalt Slabs Suitable for Characterisation. Sydney: Standards Australia.
9. Australian Standard. (1995). Methods of Sampling and Testing Asphalt (Vol. AS 2891.2.1). Sydney: Standards Australia.
10. Austroads, Guide to Pavement Technology Part 2: Pavement Structural Design, ISBN 978-1-921991-11-0, Sydney, Australia, 2012.
11. Shami, H, I., Lai, J, S., D'angelo J, A, and Harman, T. P. (1997). Development of Temperature-Effect Model for Predicting Rutting of Asphalt Mixtures Using Georgia Loaded Wheel Tester. TRANSPORTATION RESEARCH RECORD.
12. Yildirim, Y., Jayawickrama, P., Hossain, M., Alhabshi, A., Yildirim, C., Smit, A., and Little, D. (2007). Hamburg Wheel-Tracking Database Analysis: Texas Department of Transportation.
13. Francken, L. Pavement Deformation Law of Bituminous Road Mixes in Repaeted Load Triaxial Compression. Proceedings of the fourth International Conference on the Structural Design of Asphalt Pavements, Vol I. The University of Michigan, Ann Arbor, Mich., 1977: 483-496.
14. Biligiri, K. P., Kaloush, K. E., Mamlouk, M. S., and Witczak, M. W. (2007). Rational Modeling of Tertiary Flow for Asphalt Mixtures. Transportation Research Record: Journal of the Transportation Research Board, 63-72.

The invention claimed is:

1. A rut testing apparatus for testing the susceptibility of a pavement specimen to rutting, the apparatus comprising:
a specimen holder for supporting the specimen to be tested, the specimen holder arranged to support the specimen from below and to support two opposite ends of the specimen, the specimen holder arranged so that one or more lateral sides of the specimen are substantially unsupported or supported by a moveable support member to allow the specimen to deform in a lateral direction that is transverse to a direction that extends between the opposite ends for substantially an entire test;
a wheel that is arranged to move along at least part of the specimen in the direction that extends between the opposite ends; and
a sensor to determine deformation of the specimen in the lateral direction.

2. A rut testing apparatus according to claim 1, wherein the specimen holder is arranged so that two lateral sides of the specimen are substantially unsupported during testing.

3. A rut testing apparatus according to claim 2, comprising a second sensor associated with the second lateral side to determine deformation of the specimen in the lateral direction.

4. A rut testing apparatus according to claim 1, wherein the specimen holder comprises a first moveable support member to support a first lateral side of the specimen, the first movable support member arranged to allow deformation of the specimen in the lateral direction.

5. A rut testing apparatus according to claim 4, wherein the position of the first moveable support member is controlled to provide substantially constant pressure to the first lateral side of the specimen during testing.

6. A rut testing apparatus according to claim 4, wherein the specimen holder comprises a fixed support member to support a second opposite lateral side of the specimen.

7. A rut testing apparatus according to claim 4, wherein the specimen holder comprises a second moveable support member to support a second opposite lateral side of the specimen, the second moveable support member arranged to allow deformation of the specimen in the lateral direction.

8. A rut testing apparatus according to claim 7, comprising a second sensor associated with the second lateral side to determine deformation of the specimen in the lateral direction.

9. A rut testing apparatus according to claim 1, wherein the specimen holder comprises a first end moveable support member to support a first end of the specimen, the first end moveable support member arranged to allow deformation of the specimen in the direction that extends between the opposite ends.

10. A rut testing apparatus according to claim 9, wherein the specimen holder comprises a fixed end support member to support a second opposite end of the specimen.

11. A rut testing apparatus according to claim 9, wherein the specimen holder comprises a second end moveable support member to support a second opposite end of the specimen, the second end moveable support member arranged to allow deformation of the specimen in the direction that extends between the opposite ends.

12. A rut testing apparatus according to claim 9, wherein the position of the first end moveable support member is controlled to provide substantially constant pressure to the first end of the specimen during testing.

13. A rut testing apparatus according to claim 1, comprising a sensor to determine deformation of the specimen in a direction that is generally orthogonal to the direction that extends between the opposite ends and to the lateral direction.

14. A rut testing apparatus according to claim 1, comprising a processor configured to provide a graphical representation of deformation in the lateral direction and/or in a direction that is generally orthogonal to the direction that extends between the opposite ends and to the lateral direction, wherein the graphical representation shows the rate of change of permanent deformation in the lateral direction and/or in the direction that is generally orthogonal to the direction that extends between the opposite ends and to the lateral direction.

15. A rut testing apparatus according to claim 14, wherein the graphical representation shows the number of cycles at which permanent deformation in both directions progresses at the same rate.

16. A rut testing apparatus according to claim 15, wherein the processor is configured to determine or estimate permanent deformation in the direction that is generally orthogonal to the direction that extends between the opposite ends and to the lateral direction, based on the determined permanent deformation in the lateral direction.

17. A rut testing apparatus according to claim 1, comprising a processor configured to determine the extent of deformation in the lateral direction and/or in a direction that is generally orthogonal to the direction that extends between the opposite ends and to the lateral direction, wherein the processor is configured to determine the rate of change of permanent deformation in the lateral direction and/or in the direction that is generally orthogonal to the direction that extends between the opposite ends and to the lateral direction.

18. A rut testing apparatus according to claim 17, wherein the processor is configured to determine the number of cycles at which permanent deformation in both directions progresses at the same rate.

19. A rut testing apparatus according to claim 1, wherein the lateral direction is substantially orthogonal to the direction that extends between the opposite ends.

20. A method of testing the susceptibility of a pavement specimen to rutting, the method comprising:
　supporting a pavement specimen in a specimen holder, the specimen holder arranged to support the specimen from below and to support two opposite ends of the specimen, the specimen holder arranged so that one or more lateral sides of the specimen are substantially unsupported or supported by a moveable support member to allow the specimen to deform in a lateral direction that is transverse to a direction that extends between the opposite ends for substantially an entire test;
　moving a wheel along at least part of the specimen in the direction that extends between the opposite ends; and
　measuring deformation of the specimen in the lateral direction.

* * * * *